(12) United States Patent
Kim et al.

(10) Patent No.: US 11,515,476 B2
(45) Date of Patent: Nov. 29, 2022

(54) INK COMPOSITION AND METHOD FOR MANUFACTURING ORGANIC LIGHT EMITTING DEVICE

(71) Applicant: LG Chem, Ltd., Seoul (KR)

(72) Inventors: Mi Kyoung Kim, Daejeon (KR); Ji Young Jung, Daejeon (KR)

(73) Assignee: LG Chem, Ltd.

( * ) Notice: Subject to any disclaimer, the term of this patent is extended or adjusted under 35 U.S.C. 154(b) by 474 days.

(21) Appl. No.: 16/641,479

(22) PCT Filed: Mar. 15, 2019

(86) PCT No.: PCT/KR2019/003007
§ 371 (c)(1),
(2) Date: Feb. 24, 2020

(87) PCT Pub. No.: WO2019/177410
PCT Pub. Date: Sep. 19, 2019

(65) Prior Publication Data
US 2021/0050523 A1 Feb. 18, 2021

(30) Foreign Application Priority Data
Mar. 16, 2018 (KR) .......... 10-2018-0030985

(51) Int. Cl.
*C09D 11/033* (2014.01)
*C07C 211/61* (2006.01)
(Continued)

(52) U.S. Cl.
CPC ........ *H01L 51/0007* (2013.01); *C07C 211/61* (2013.01); *C07C 217/94* (2013.01); *C09D 11/033* (2013.01); *C09D 11/037* (2013.01); *C09D 11/322* (2013.01); *C09D 11/36* (2013.01); *C09D 11/50* (2013.01); *C09K 11/06* (2013.01); *H01L 51/006* (2013.01);
(Continued)

(58) Field of Classification Search
CPC .. C07C 211/61; C07C 217/94; C07C 2603/18
See application file for complete search history.

(56) References Cited

U.S. PATENT DOCUMENTS

2015/0094437 A1 4/2015 Caille et al.
2017/0148993 A1 5/2017 Funahashi et al.
(Continued)

FOREIGN PATENT DOCUMENTS

EP 2610240 A1 7/2013
JP 2008219053 A 9/2008
(Continued)

OTHER PUBLICATIONS

International Search Report for Application No. PCT/KR2019/003007 dated Jun. 25, 2019, 3 pages.
(Continued)

*Primary Examiner* — Vu A Nguyen
(74) *Attorney, Agent, or Firm* — Lerner, David, Littenberg, Krumholz & Mentlik, LLP

(57) ABSTRACT

The present specification relates to an ink composition including: a compound represented by Formula 1; and a solvent represented by the Formula 2, and a method for manufacturing an organic light emitting device formed by using the ink composition.

18 Claims, 1 Drawing Sheet

(51) Int. Cl.
  *C09K 11/06* (2006.01)
  *H01L 51/00* (2006.01)
  *H01L 51/50* (2006.01)
  *C07C 217/94* (2006.01)
  *C09D 11/037* (2014.01)
  *C09D 11/322* (2014.01)
  *C09D 11/36* (2014.01)
  *C09D 11/50* (2014.01)

(52) U.S. Cl.
  CPC .. *C07C 2603/18* (2017.05); *C09K 2211/1007* (2013.01); *C09K 2211/1011* (2013.01); *C09K 2211/1014* (2013.01); *H01L 51/0058* (2013.01); *H01L 51/5012* (2013.01); *H01L 51/5056* (2013.01); *H01L 51/5072* (2013.01); *H01L 51/5088* (2013.01); *H01L 51/5092* (2013.01)

(56) References Cited

U.S. PATENT DOCUMENTS

| | | |
|---|---|---|
| 2018/0030297 A1 | 2/2018 | Oda et al. |
| 2018/0155616 A1 | 6/2018 | Bealle et al. |
| 2018/0375028 A1 | 12/2018 | Park et al. |
| 2019/0237669 A1 | 8/2019 | Kang et al. |

FOREIGN PATENT DOCUMENTS

| | | | | |
|---|---|---|---|---|
| JP | 2018021095 A | 2/2018 | | |
| KR | 20090114716 A | 11/2009 | | |
| KR | 20110125369 A | 11/2011 | | |
| KR | 20140107594 A | 9/2014 | | |
| KR | 20140132562 A | 11/2014 | | |
| KR | 20150093995 A | * 8/2015 | ........... | C07D 403/14 |
| KR | 20150093995 A | 8/2015 | | |
| KR | 20160041124 A | 4/2016 | | |
| KR | 20160134658 A | 11/2016 | | |
| KR | 20180017138 A | 2/2018 | | |
| WO | 2017102048 A1 | 6/2017 | | |
| WO | WO-2017102048 A1 | * 6/2017 | ............ | C09D 11/36 |
| WO | 2018159937 A1 | 9/2018 | | |
| WO | 2020067800 A1 | 4/2020 | | |

OTHER PUBLICATIONS

Extended European Search Report including Written Opinion for Application No. EP19767490.6, dated Oct. 20, 2020, pp. 1-6.

\* cited by examiner

[Figure 1]
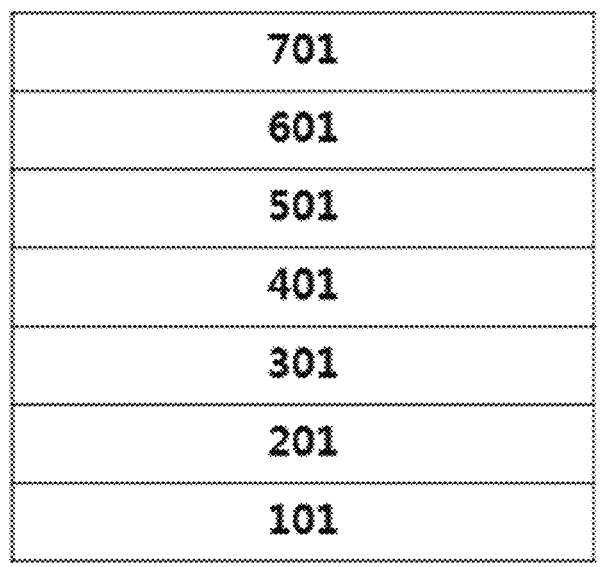
[Figure 2]
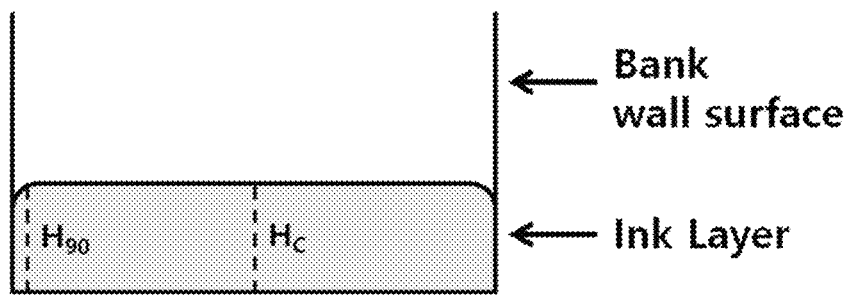

INK COMPOSITION AND METHOD FOR MANUFACTURING ORGANIC LIGHT EMITTING DEVICE

CROSS-REFERENCE TO RELATED APPLICATIONS

This application is a national phase entry under 35 U.S.C. § 371 of International Application No. PCT/KR2019/003007 filed Mar. 15, 2019, which claims priority from Korean Patent Application No. 10-2018-0030985 filed Mar. 16, 2018, all of which are incorporated herein by reference.

TECHNICAL FIELD

The present specification relates to an ink composition and a method for manufacturing an organic light emitting device.

BACKGROUND ART

A deposition process in the related art has a disadvantage in that it is difficult to manufacture a red-green-blue (RGB) type OLED display because a mask sagging phenomenon occurs as the area of the display increases. However, a solution process such as inkjet printing has an advantage in that a RGB type pattern may be formed even in a large area of a display, and all RGBs may be formed with a one-time process only.

Further, recently, as the amount of material consumed has been minimized, an apparatus has been miniaturized, or the resolution of a display has been increased, the formation of a precise pattern has been required, so that a method for manufacturing an organic light emitting device by an economical and stable inkjet printing process has drawn attention.

An ink composition used in an inkjet printing process needs to enable a stable discharge, prevent a functional layer material such as a charge transport material or a light emitting material and a solvent from being phase-separated, and enable a uniform film to be formed during the formation of the film.

In the related art, solvents of ethers having a relatively low polarity or solvents of hydrocarbons have been frequently used in the ink composition, and for example, solvents such as phenoxytoluene and cyclohexylbenzene have been used. However, when the solvent is used as a main solvent, there are problems in that the process time is prolonged because there is a limitation in increasing the solid content of ink due to the low solubility for the functional layer material, and a stable film cannot be formed because the phase separation occurs during the drying.

Further, when the solubility of a solvent for a functional layer material is low, the number of drops dropped onto a pixel is increased in order to obtain a desired thickness because the amount of functional layer material which may be dissolved in ink is limited, so that it is difficult not only to obtain a flat profile, but also to obtain a desired thickness.

In addition, a solvent used in an ink composition needs to have high solubility for a functional layer material and have a high boiling point in order to prevent a problem in that a nozzle part is dried. For example, cyclohexanone in the related art corresponds to a solvent having good solubility, but has a low boiling point, so that when cyclohexanone is used in an ink composition, cyclohexanone is not appropriate for an inkjet process because a nozzle part is dried.

Therefore, there is a need in the art for developing an ink composition including a solvent having excellent solubility for a functional material and a high boiling point.

DETAILED DESCRIPTION OF INVENTION

Technical Problem

The present specification has been made in an effort to provide an ink composition that may be used in an organic light emitting device and a method for manufacturing an organic light emitting device using the same.

Technical Solution

The present specification provides an ink composition including: a compound represented by the following Formula 1; and a solvent represented by the following Formula 2.

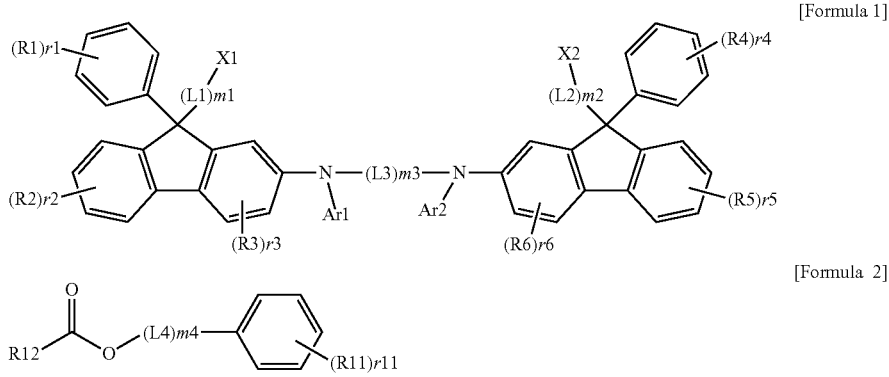

[Formula 1]

[Formula 2]

In Formulae 1 and 2,

L1, L2, and L4 are the same as or different from each other, and are each independently a direct bond; a substituted or unsubstituted alkylene group; a substituted or unsubstituted arylene group; or a substituted or unsubstituted heteroarylene group, L3 is a substituted or unsubstituted arylene group; or a substituted or unsubstituted heteroarylene group, X1 and X2 are the same as or different from each other, and are each independently a photocurable group or a thermosetting group, Ar1 and Ar2 are the same as or different from each other, and are each independently a substituted or unsubstituted aryl group; or a substituted or unsubstituted heteroaryl group, R1 to R6 are the same as or different from each other, and are each independently hydrogen; deuterium; a substituted or unsubstituted alkyl group; a substituted or unsubstituted alkoxy group; a substituted or unsubstituted aryl group; or a substituted or unsubstituted heteroaryl group, R11 is hydrogen; deuterium; or a substituted or unsubstituted alkyl group, R12 is a substituted or unsubstituted alkyl group having 2 or more carbon atoms, m1 to m4 are an integer from 1 to 6, when m1 to m4 are each 2 or more, two or more L1's to L4's are each the same as or different from each other, r1, r4, and r11 are an integer from 1 to 5, r2 and r5 are an integer from 1 to 4, r3 and r6 are an integer from 1 to 3, and when r1 to r6 and r11 are each 2 or more, two or more R1's to R6's and R11's are each the same as or different from each other.

The present specification provides a method for manufacturing an organic light emitting device, the method including: preparing a substrate; forming a first electrode or a second electron on the substrate; forming an organic material layer having one or more layers on the first electrode or the second electrode; and forming a second electrode or a first electrode on the organic material layer, in which the forming of the organic material layer includes forming an organic material layer having one or more layers by using the ink composition.

Advantageous Effects

In an ink composition according to an exemplary embodiment of the present specification, the solubility of a solvent for a functional layer material is high, so that it is possible to increase the content of the functional layer material in the ink composition and to enhance the stability of the ink composition due to the increase in content of the functional layer material in the ink composition. That is, a flat film may be formed because precipitation or phase separation of the functional layer material does not occur.

Further, a uniform film may be formed by controlling the evaporation rate in the process of drying the ink composition due to low vapor pressure characteristics.

BRIEF DESCRIPTION OF DRAWINGS

FIG. 1 illustrates an example of an organic light emitting device according to an exemplary embodiment of the present specification.

FIG. 2 illustrates the evaluation of flatness of film.

101: Substrate
201: Anode
301: Hole injection layer
401: Hole transport layer
501: Light emitting layer
601: Electron transport layer
701: Cathode

BEST MODE

An ink composition used in an inkjet printing process needs to enable a stable discharge, prevent a functional layer material such as a charge transport material or a light emitting material and a solvent from being phase-separated, and enable a uniform film to be formed during the formation of the film.

In the related art, solvents of ethers having a relatively low polarity and solvents of hydrocarbons have been frequently used in the ink composition, and for example, solvents such as phenoxytoluene and cyclohexylbenzene have been used. However, when the solvent is used as a main solvent, there are problems in that the process time is prolonged due to the limitation because there is a limitation in increasing the solid content of ink due to the low solubility for the functional layer material, and a stable film cannot be formed because the phase separation occurs during the drying.

Further, when the solubility of a solvent for a functional layer material is low, the number of drops dropped onto a pixel is increased in order to obtain a desired thickness because the amount of functional layer material which may be dissolved in ink is limited, so that it is difficult not only to obtain a flat profile, but also to obtain a desired thickness.

In addition, a solvent used in an ink composition needs to have high solubility for a functional layer material and have a high boiling point in order to prevent a problem in that a nozzle part is dried. For example, cyclohexanone in the related art corresponds to a solvent having good solubility, but has a low boiling point, so that when cyclohexanone is used in an ink composition, cyclohexanone is not appropriate for an inkjet process because a nozzle part is dried.

In an ink composition according to an exemplary embodiment of the present specification, the solubility of a solvent for a functional layer material is high, so that it is possible to increase the content of the functional layer material in the ink composition and to enhance the stability of the ink composition due to the increase in content of the functional layer material in the ink composition. That is, a flat film may be formed because precipitation or phase separation of the functional layer material does not occur.

Further, a uniform film may be formed by controlling the evaporation rate in the process of drying the ink composition due to low vapor pressure characteristics.

The present specification provides the compound represented by Formula 1.

In general, since an arylamine-based single molecule used in an organic light emitting device for a solution process does not itself have resistance to a solvent in the next process, a curing group needs to be introduced into the arylamine-based single molecule which can be used in OLED device for a solution process. A fluorene-based compound to which an amine group is bonded, which is represented by Formula 1 of the present specification, may reduce steric hindrance around a curing group as an appropriate distance is maintained between the curing group and fluorene due to a linker. Accordingly, the mobility of the curing group itself may be increased to efficiently perform a curing reaction during light and heat treatments on a thin film, and to form a thin film having excellent solvent resistance.

Further, when a styrene group or an ethenyl group as a curing agent is bonded to the fluorene-based compound according to an exemplary embodiment of the present specification, it is possible to reduce the interference with the interaction on a thin film in a part which is connected to a fluorene to which a cured product is bonded and an arylamine-based single molecular core skeleton by introducing a curing group into the position of No. 9 carbon of fluorene in which the conjugation with the core structure of fluorene is broken. In addition, it is possible not only to minimize an undesirable effect on the molecular orbital function of the core skeleton, but also to manufacture an organic light emitting device having a longer service life.

Furthermore, the present specification provides the solvent represented by Formula 2.

The solvent represented by Formula 2 has higher solubility and a higher boiling point than solvents in the related art, so that it is possible to increase the content of the compound represented by Formula 1, which is a functional layer material in the ink composition. Accordingly, since the stability of the ink composition may be enhanced, precipitation or phase separation of the functional layer material does not occur, so that it possible to effectively form a flat film.

Hereinafter, the present specification will be described in more detail.

When one member is disposed "on" another member in the present specification, this includes not only a case where the one member is brought into contact with another member, but also a case where still another member is present between the two members.

When one part "includes" one constituent element in the present specification, unless otherwise specifically described, this does not mean that another constituent element is excluded, but means that another constituent element may be further included.

Examples of the substituents in the present specification will be described below, but are not limited thereto.

In the present specification,

means a moiety to be linked.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a nitrile group; a nitro group; a hydroxyl group; an alkoxy group; a silyl group; an alkyl group; a cycloalkyl group; an amine group; an aryl group; and a heterocyclic group including one or more of N, O, S, Se, and Si atoms, being substituted with a substituent to which two or more substituents among the substituents exemplified above are linked, or having no substituent.

In the present specification, examples of a halogen group include fluorine, chlorine, bromine or iodine.

In the present specification, an alkyl group may be straight-chained or branch-chained, and the number of carbon atoms thereof is not particularly limited, but is preferably 1 to 50, and more preferably 1 to 30. Specific examples thereof include methyl, ethyl, propyl, n-propyl, isopropyl, butyl, n-butyl, isobutyl, tert-butyl, sec-butyl, 1-methylbutyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 4-methylhexyl, 5-methylhexyl, and the like, but are not limited thereto.

In the present specification, a cycloalkyl group is not particularly limited, but has preferably 3 to 60 carbon atoms, and more preferably 3 to 30 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an alkoxy group may be straight-chained, branched, or cyclic. The carbon number of the alkoxy group is not particularly limited, but is preferably 1 to 20 carbon atoms, and more preferably 1 to 10 carbon atoms. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, a silyl group includes Si and is a substituent to which the Si atom is directly linked as a radical, and is represented by —SiR$_{201}$R$_{202}$R$_{203}$, and R$_{201}$ to R$_{203}$ are the same as or different from each other, and may be each independently a substituent composed of at least one of hydrogen; deuterium; a halogen group; an alkyl group; an alkenyl group; an alkoxy group; a cycloalkyl group; an aryl group; and a heterocyclic group. Specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, when an aryl group is a monocyclic aryl group, the number of carbon atoms thereof is not particularly limited, but is preferably 6 to 50, and more preferably 6 to 30. Specific examples of the monocyclic aryl group include a phenyl group, a biphenyl group, a terphenyl group, a quarterphenyl group, and the like, but are not limited thereto.

When the aryl group is a polycyclic aryl group, the number of carbon atoms thereof is not particularly limited, but is preferably 10 to 50, and more preferably 10 to 30. Specific examples of the polycyclic aryl group include a naphthyl group, an anthracenyl group, a phenanthryl group, pyrenyl group, a perylenyl group, a triphenylene group, a chrysenyl group, a fluorenyl group, and the like, but are not limited thereto.

In the present specification, the fluorenyl group may be substituted, and adjacent substituents may be bonded to each other to form a ring.

When the fluorenyl group is substituted, the substituent may be

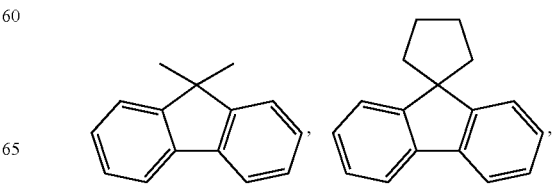

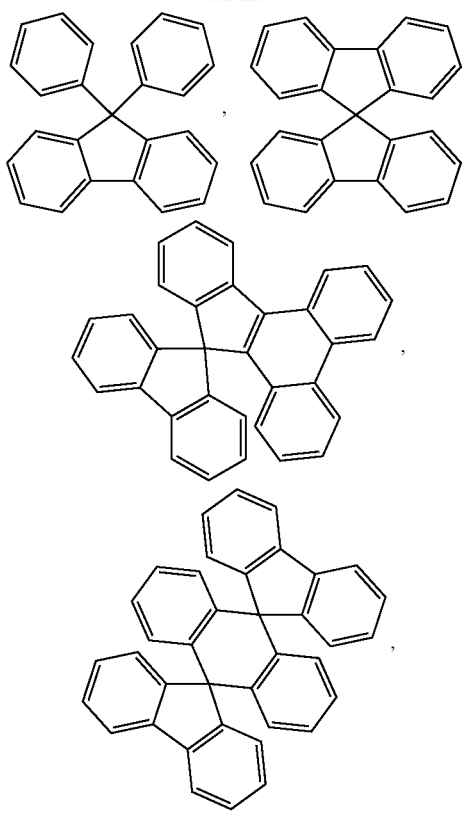

and the like, but is not limited thereto.

In the present specification, a heterocyclic group includes one or more of N, O, S, Si, and Se as a heteroatom, and the number of carbon atoms thereof is not particularly limited, but is preferably 2 to 60, and more preferably 2 to 30. Examples of the heterocyclic group include a thiophene group, a furan group, a pyrrole group, an imidazole group, a triazole group, an oxazole group, an oxadiazole group, a triazole group, a pyridine group, a bipyridine group, a pyrimidine group, a triazine group, an acridine group, a pyridazine group, a pyrazine group, a quinoline group, a quinazoline group, a quinoxaline group, a phthalazine group, a pteridine group, a pyrido pyrimidine group, a pyrido pyrazine group, a pyrazino pyrazine group, an isoquinoline group, an indole group, a pyrido indole group, indeno pyrimidine (5H-indeno pyrimidine), a carbazole group, a benzoxazole group, a benzimidazole group, a benzothiazole group, a benzocarbazole group, a benzothiophene group, a dibenzothiophene group, a benzofuran group, a dibenzofuran group, a phenanthroline group, a thiazolyl group, an isoxazolyl group, an oxadiazolyl group, a thiadiazolyl group, and the like, but are not limited thereto.

In the present specification, a heteroaryl group may be selected from the examples of the heterocyclic group except for an aromatic heteroaryl group, but is not limited thereto.

In the present specification, an amine group is represented by —$NR_{206}R_{207}$, and $R_{206}$ and $R_{207}$ are the same as or different from each other, and may be each independently a substituent composed of at least one of hydrogen, deuterium, a halogen group, an alkyl group, an alkenyl group, an alkoxy group, a cycloalkyl group, an aryl group, and a heterocyclic group. For example, the amine group may be selected from the group consisting of —$NH_2$, a monoalkylamine group, a dialkylamine group, an N-alkylarylamine group, a monoarylamine group, a diarylamine group, an N-arylheteroarylamine group, an N-alkylheteroarylamine group, a monoheteroarylamine group, and a diheteroarylamine group, and the number of carbon atoms thereof is not particularly limited, but is preferably 1 to 30, and more preferably 1 to 20. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a ditolylamine group, an N-phenyltolylamine group, a triphenylamine group, an N-phenylbiphenylamine group, an N-phenylnaphthylamine group, an N-biphenylnaphthylamine group; an N-naphthylfluorenylamine group; an N-phenylphenanthrenylamine group, an N-biphenylphenanthrenylamine group, an N-phenylfluorenylamine group, an N-phenyl terphenylamine group, an N-phenanthrenylfluorenylamine group, an N-biphenylfluorenylamine group, and the like, but are not limited thereto.

In the present specification, examples of an arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include a monocyclic aryl group, a polycyclic aryl group, or both a monocyclic aryl group and a polycyclic aryl group. For example, the aryl group in the arylamine group may be selected from the above-described examples of the aryl group.

In the present specification, an alkylene group means a group having two bonding positions in an alkyl group, that is, a divalent group. The above-described description on the alkyl group may be applied to the alkylene group, except for a divalent alkylene group.

In the present specification, an arylene group means a group having two bonding positions in an aryl group, that is, a divalent group. The above-described description on the aryl group may be applied to the arylene group, except for a divalent arylene group.

In the present specification, a heteroarylene group means a group having two bonding positions in a heteroaryl group, that is, a divalent group. The above-described description on the heteroaryl group may be applied to the heteroarylene group, except for a divalent heteroarylene group.

In an exemplary embodiment of the present specification, L1, L2, and L4 are the same as or different from each other, and are each independently a direct bond; a substituted or unsubstituted alkylene group; a substituted or unsubstituted arylene group; or a substituted or unsubstituted heteroarylene group.

In an exemplary embodiment of the present specification, L1 is a direct bond.

In an exemplary embodiment of the present specification, L2 is a direct bond.

In an exemplary embodiment of the present specification, L1 and L2 are the same as or different from each other, and are each independently a substituted or unsubstituted alkylene group having 1 to 20 carbon atoms.

In an exemplary embodiment of the present specification, L1 and L2 are the same as or different from each other, and are each independently a substituted or unsubstituted alkylene group having 1 to 10 carbon atoms.

In an exemplary embodiment of the present specification, L1 is a substituted or unsubstituted hexylene group, a substituted or unsubstituted heptylene group, or a substituted or unsubstituted octylene group.

In an exemplary embodiment of the present specification, L1 is a hexylene group.

In an exemplary embodiment of the present specification, L1 is a heptylene group.

In an exemplary embodiment of the present specification, L1 is an octylene group.

In an exemplary embodiment of the present specification, L2 is a substituted or unsubstituted hexylene group, a substituted or unsubstituted heptylene group, or a substituted or unsubstituted octylene group.

In an exemplary embodiment of the present specification, L2 is a hexylene group.

In an exemplary embodiment of the present specification, L2 is a heptylene group.

In an exemplary embodiment of the present specification, L2 is an octylene group.

In an exemplary embodiment of the present specification, L4 is a direct bond.

In an exemplary embodiment of the present specification, L4 is a substituted or unsubstituted alkylene group having 1 to 10 carbon atoms.

In an exemplary embodiment of the present specification, L4 is a substituted or unsubstituted methylene group, a substituted or unsubstituted ethylene group, a substituted or unsubstituted propylene group, a substituted or unsubstituted butylene group, a substituted or unsubstituted pentylene group, or a substituted or unsubstituted hexylene group.

In an exemplary embodiment of the present specification, L4 is a methylene group.

In an exemplary embodiment of the present specification, L4 is an ethylene group.

In an exemplary embodiment of the present specification, L3 is a substituted or unsubstituted arylene group; or a substituted or unsubstituted heteroarylene group.

In an exemplary embodiment of the present specification, L3 is a substituted or unsubstituted arylene group having 6 to 30 carbon atoms.

In an exemplary embodiment of the present specification, L3 is a substituted or unsubstituted phenylene group, a substituted or unsubstituted biphenylene group, a substituted or unsubstituted terphenylene group; a substituted or unsubstituted naphthylene group, a substituted or unsubstituted phenanthrylene group, a substituted or unsubstituted triphenylene group, or a substituted or unsubstituted fluorenylene group.

In an exemplary embodiment of the present specification, L3 is a biphenylene group.

In an exemplary embodiment of the present specification, L3 is a substituted or unsubstituted heteroarylene group having 2 to 30 carbon atoms.

In an exemplary embodiment of the present specification, X1 and X2 are the same as or different from each other, and are each independently a photocurable group or a thermosetting group.

In an exemplary embodiment of the present specification, X1 and X2 are any one selected from the following structures.

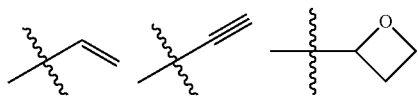

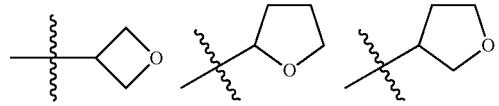

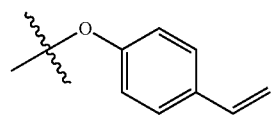

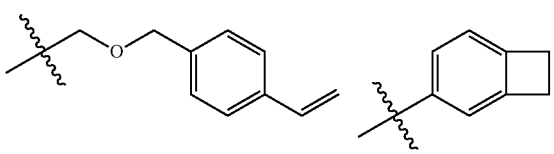

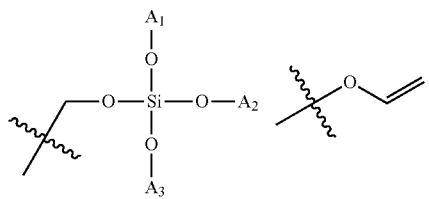

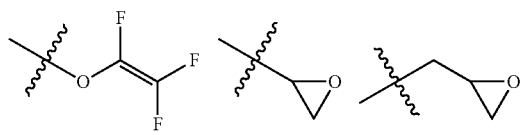

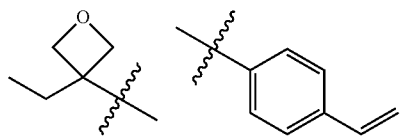

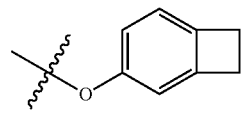

In the structures, $A_1$ to $A_3$ are the same as or different from each other, and are each independently a substituted or unsubstituted alkyl group having 1 to 6 carbon atoms.

In an exemplary embodiment of the present specification, Ar1 and Ar2 are the same as or different from each other, and are each independently a substituted or unsubstituted aryl group; or a substituted or unsubstituted heteroaryl group.

In an exemplary embodiment of the present specification, Ar1 and Ar2 are the same as or different from each other, and are each independently a substituted or unsubstituted aryl group having 6 to 30 carbon atoms.

In an exemplary embodiment of the present specification, Ar1 is a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, a substituted or unsubstituted triphenylene group, or a substituted or unsubstituted fluorenyl group.

In an exemplary embodiment of the present specification, Ar1 is a phenyl group.

In an exemplary embodiment of the present specification, Ar1 is a biphenyl group.

In an exemplary embodiment of the present specification, Ar1 is a naphthyl group.

In an exemplary embodiment of the present specification, Ar2 is a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, a substituted or unsubstituted triphenyl group, or a substituted or unsubstituted fluorenyl group.

In an exemplary embodiment of the present specification, Ar2 is a phenyl group.

In an exemplary embodiment of the present specification, Ar2 is a biphenyl group.

In an exemplary embodiment of the present specification, Ar2 is a naphthyl group.

In an exemplary embodiment of the present specification, R1 to R6 are the same as or different from each other, and are each independently hydrogen; deuterium; a substituted or unsubstituted alkyl group; a substituted or unsubstituted alkoxy group; a substituted or unsubstituted aryl group; or a substituted or unsubstituted heteroaryl group.

In an exemplary embodiment of the present specification, R1 to R6 are the same as or different from each other, and are each independently a substituted or unsubstituted alkyl group having 1 to 10 carbon atoms.

In an exemplary embodiment of the present specification, R1 to R6 are the same as or different from each other, and are each independently a substituted or unsubstituted methyl group, a substituted or unsubstituted ethyl group, a substituted or unsubstituted propyl group, a substituted or unsubstituted isopropyl group, or a substituted or unsubstituted tert-butyl group.

In an exemplary embodiment of the present specification, R1 is a methyl group.

In an exemplary embodiment of the present specification, R4 is a methyl group.

In an exemplary embodiment of the present specification, R1 to R6 are each hydrogen.

In an exemplary embodiment of the present specification, R11 is hydrogen; deuterium; or a substituted or unsubstituted alkyl group.

In an exemplary embodiment of the present specification, R11 is hydrogen.

In an exemplary embodiment of the present specification, R11 is a substituted or unsubstituted alkyl group having 1 to 10 carbon atoms.

In an exemplary embodiment of the present specification, R11 is a substituted or unsubstituted methyl group, a substituted or unsubstituted ethyl group, or a substituted or unsubstituted propyl group.

In an exemplary embodiment of the present specification, R11 is a methyl group.

In an exemplary embodiment of the present specification, R12 is a substituted or unsubstituted alkyl group having 2 or more carbon atoms.

In an exemplary embodiment of the present specification, R12 is a substituted or unsubstituted alkyl group having 2 to 20 carbon atoms.

In an exemplary embodiment of the present specification, R12 is a substituted or unsubstituted alkyl group having 2 to 10 carbon atoms.

In an exemplary embodiment of the present specification, R12 is a substituted or unsubstituted ethyl group, a substituted or unsubstituted propyl group, a substituted or unsubstituted butyl group, a substituted or unsubstituted pentyl group, a substituted or unsubstituted hexyl group, a substituted or unsubstituted heptyl group, a substituted or unsubstituted octyl group, or a substituted or unsubstituted nonyl group.

In an exemplary embodiment of the present specification, R12 is an ethyl group.

In an exemplary embodiment of the present specification, R12 is a propyl group.

In an exemplary embodiment of the present specification, R12 is a butyl group.

In an exemplary embodiment of the present specification, R12 is a pentyl group.

In an exemplary embodiment of the present specification, R12 is a hexyl group.

In an exemplary embodiment of the present specification, R12 is a heptyl group.

In an exemplary embodiment of the present specification, R12 is an octyl group.

In an exemplary embodiment of the present specification, R12 is a nonyl group.

In an exemplary embodiment of the present specification, m1 to m4 are an integer from 1 to 6, and when m1 to m4 are each 2 or more, two or more L1's to L4's are each the same as or different from each other.

In an exemplary embodiment of the present specification, m1 is 1.

In an exemplary embodiment of the present specification, m2 is 1.

In an exemplary embodiment of the present specification, m3 is 1.

In an exemplary embodiment of the present specification, m4 is 1.

In an exemplary embodiment of the present specification, r1, r4, and r11 are an integer from 1 to 5, r2 and r5 are an integer from 1 to 4, r3 and r6 are an integer from 1 to 3, and when r1 to r6 and r11 are each 2 or more, two or more R1's to R6's and R11's are each the same as or different from each other.

In an exemplary embodiment of the present specification, r1 is 2 or 5.

In an exemplary embodiment of the present specification, the compound represented by Formula 1 is any one selected from the following Compounds 1-1 to 1-6.

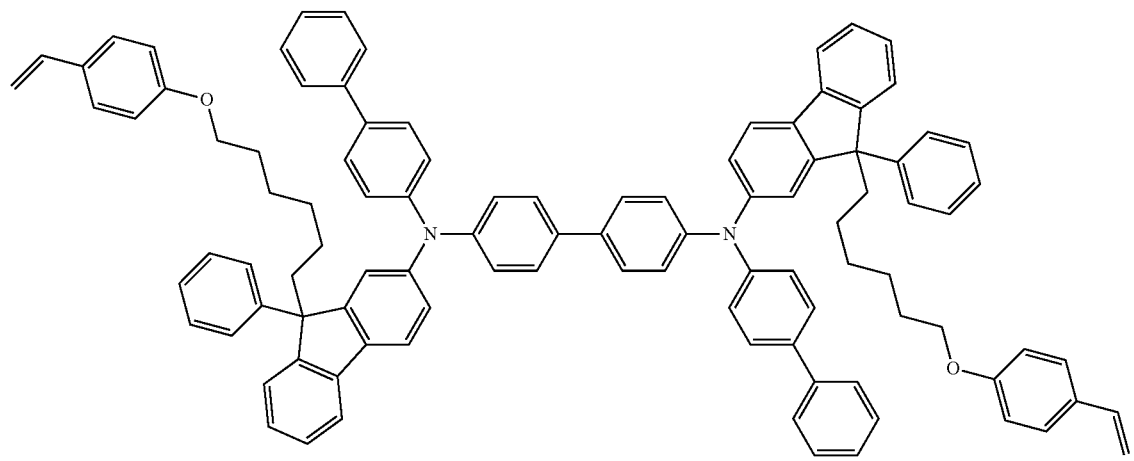
Compound 1-1
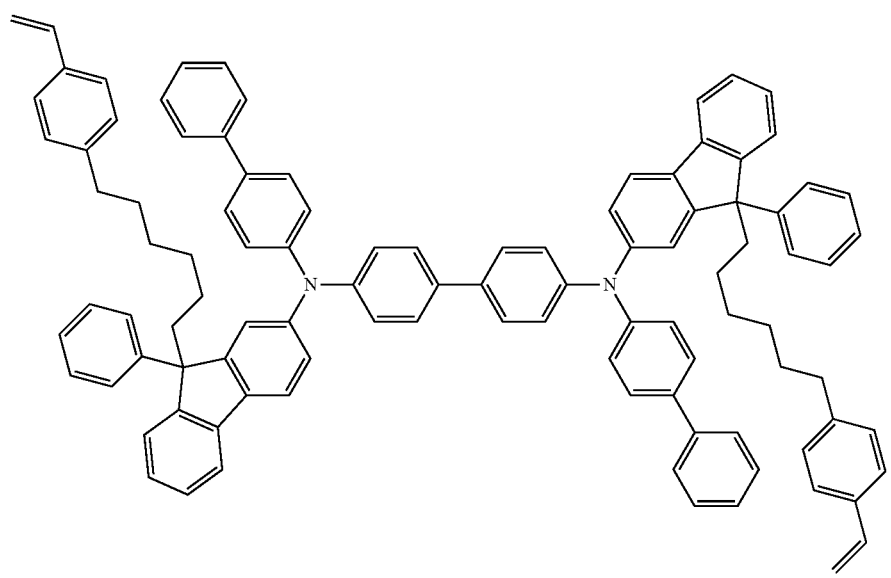
Compound 1-2
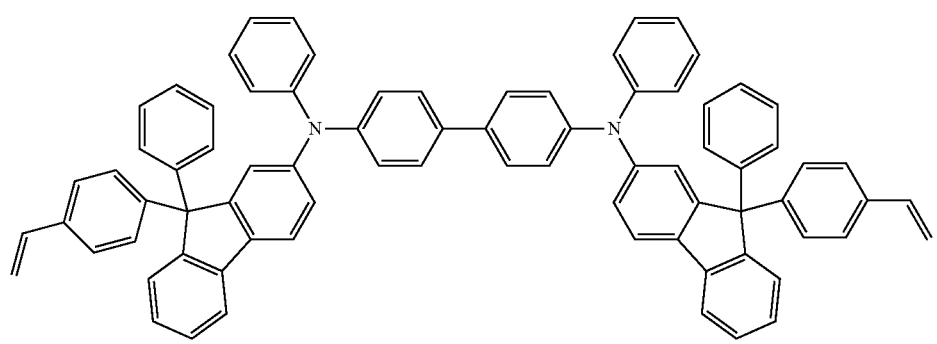
Compound 1-3

-continued
Compound 1-4
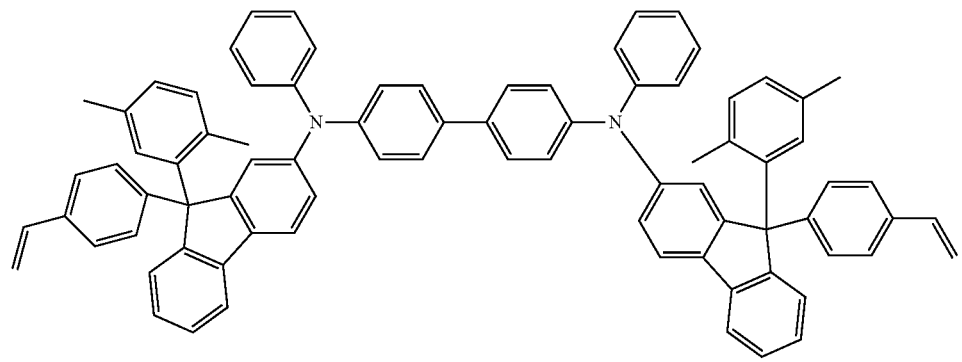
Compoound 1-5
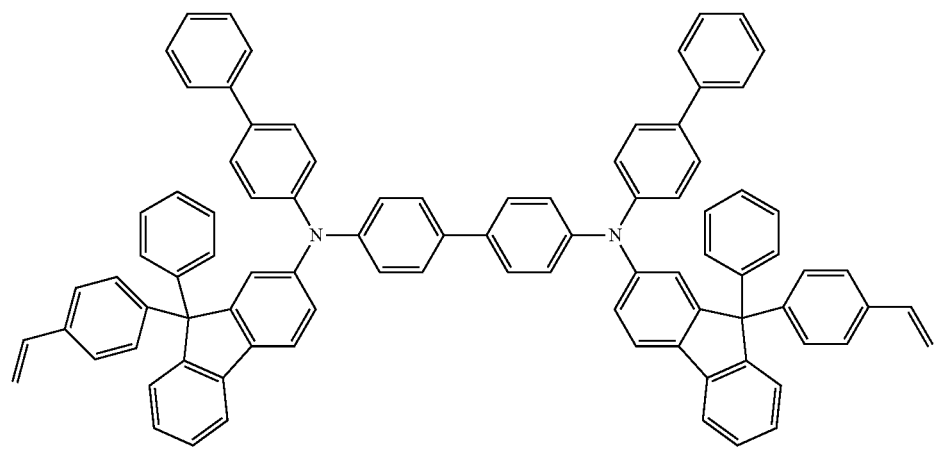
Compound 1-6
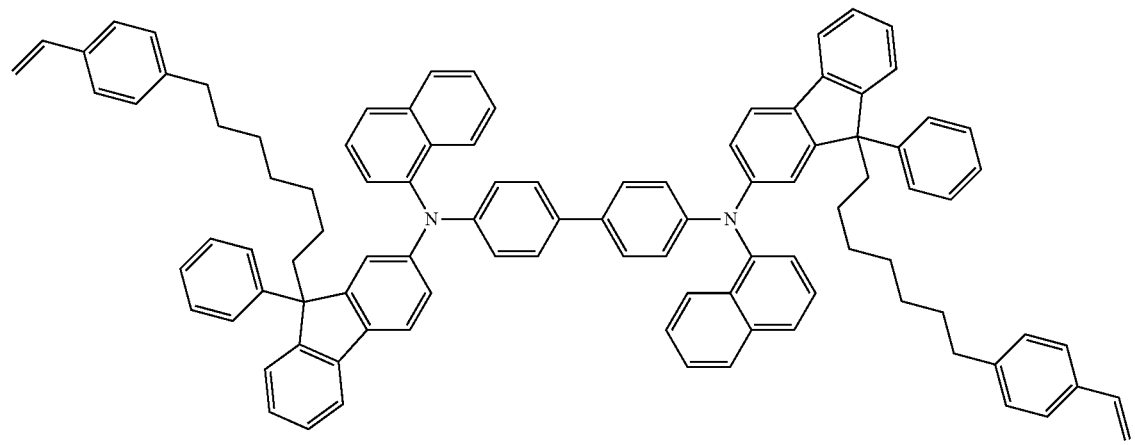
In an exemplary embodiment of the present specification, the solvent represented by Formula 2 is any one selected from the following Compounds 2-1 to 2-7.
Compound 2-1
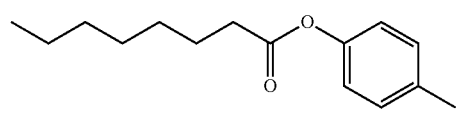
-continued
Compound 2-2
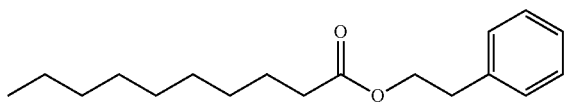
Compound 2-3
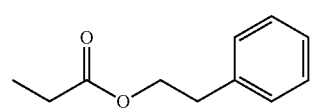

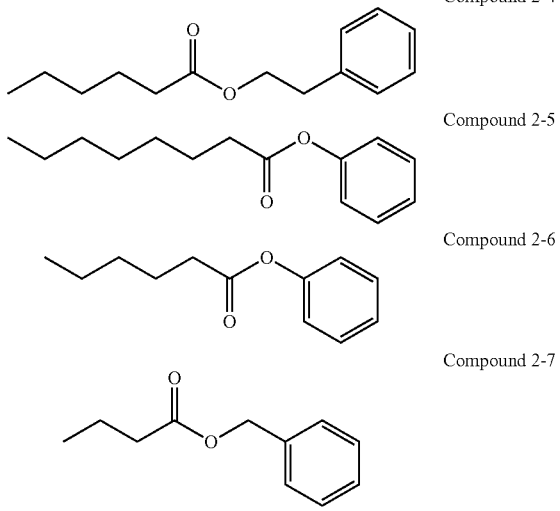

Compound 2-4

Compound 2-5

Compound 2-6

Compound 2-7

In an exemplary embodiment of the present specification, the compound represented by Formula 1 is preferably 0.1 part by weight to 10 parts by weight, and more preferably 0.5 part by weight to 5 parts by weight, based on 100 parts by weight of the total solvent. When the compound is included within the content range, a film having a desired thickness is easily obtained by adjusting the number of drops. In particular, there is an advantage in that a film having a large thickness may be obtained, and a flat film may be formed after drying.

In an exemplary embodiment of the present specification, the solubility of the compound represented by Formula 1 based on the total weight of the total solvent is 2 wt % to 15 wt % at 25° C. and 1 atm.

In an exemplary embodiment of the present specification, the ink composition has a viscosity of preferably 2 cP to 20 cP, and more preferably 3 cP to 15 cP. When the ink composition has the viscosity within the range, the ink composition may have discharge stability, so that a device is easily manufactured.

In an exemplary embodiment of the present specification, the ink composition may further include a polymer compound. When the ink composition further includes a polymer compound, ink characteristics of the ink composition may be enhanced. That is, an ink composition further including the polymer compound may provide a viscosity suitable for coating or inkjet printing, and may form a flat film.

In an exemplary embodiment of the present specification, the polymer compound has a molecular weight of 10,000 g/mol to 200,000 g/mol.

In an exemplary embodiment of the present specification, the polymer compound may further include a photo-curing group or a thermosetting group.

In an exemplary embodiment of the present specification, the ink composition may be in a liquid phase. The "liquid phase" means that the composition is in a liquid state at room temperature under atmospheric pressure.

According to an exemplary embodiment of the present specification, the ink composition may further include another solvent, in addition to the solvent represented by Formula 2, as a subsolvent during the preparation of the ink composition. The subsolvent serves to adjust the viscosity of the main solvent ink and to adjust the ink drying rate. Examples thereof include solvents such as an ether-based solvent such as phenoxytoluene and 3,4-dimethylanisole; an ester-based solvent such as methylbenzoate and dimethyl phthalate; an aromatic hydrocarbon-based solvent such as cyclohexylbenzene, methylnaphthalene, ethylnaphthalene, trimethylbenzene, isopropylnaphthalene, and mesitylene; an aliphatic hydrocarbon-based solvent such as cyclohexane, methylcyclohexane, n-pentane, n-hexane, n-heptane, n-octane, n-nonane, and n-decane; a glycol ether solvent such as diethylene glycol butyl methyl ether and triethylene glycol monobenzyl ether; a fluorine-based solvent; and an alcohol-based solvent such as methanol, ethanol, propanol, butanol, phenol, and phenyl ethyl alcohol, but are not limited thereto.

The subsolvent may be included in an amount of 0.1 wt % to 70 wt % or 0.1 wt % to 50 wt %, and preferably 1 wt % to 30 wt % based on the total solvent.

In an exemplary embodiment of the present specification, the subsolvent is an aromatic hydrocarbon-based solvent; or an alcohol-based solvent.

In an exemplary embodiment of the present specification, the subsolvent is 3-ethylbiphenyl, 2-isopropylnaphthalene, or 2-phenylethyl alcohol.

In an exemplary embodiment of the present specification, the ink composition may further include one or two or more additives selected from the group consisting of a thermal polymerization initiator and a photopolymerization initiator.

Examples of the thermal polymerization initiator include peroxides such as methyl ethyl ketone peroxide, methyl isobutyl ketone peroxide, acetyl acetone peroxide, methyl cyclohexanone peroxide, cyclohexanone peroxide, isobutyryl peroxide, 2,4-dichlorobenzoyl peroxide, bis-3,5,5-trimethylhexanoyl peroxide, lauryl peroxide, benzoyl peroxide, p-kroll benzoyl peroxide, dicumyl peroxide, 2,5-dimethyl-2,5-(t-butyl oxy)-hexane, 1,3-bis(t-butyl peroxyisopropyl) benzene, t-butyl cumyl peroxide, di-t-butyl peroxide, 2,5-dimethyl-2,5-(di-t-butyl peroxy) hexane-3, tris-(t-butyl peroxy) triazine, 1,1-di-t-butyl peroxy-3,3,5-trimethyl cyclohexane, 1,1-di-t-butylperoxy cyclohexane, 2,2-di(t-butyl peroxy) butane, 2,2-bis(4,4-t-butyl peroxy cyclohexyl)propane, t-butyl peroxy isobutyrate, di-t-butyl peroxy hexahydro terephthalate, t-butyl peroxy-3,5,5-trimethylhexate, t-butyl peroxybenzoate, and di-t-butyl peroxy trimethyl adipate; or an azo-based thermal polymerization initiator such as azobisisobutyronitrile, azobisdimethylvaleronitrile, and azobiscyclohexyl nitrile, but the examples are not limited thereto.

Examples of the photopolymerization initiator include an acetophenone-based or ketal-based photopolymerization initiator such as diethoxy acetophenone, 2,2-dimethoxy-1,2-diphenylethan-1-one, 1-hydroxy-cyclohexyl-phenyl-ketone, 4-(2-hydroxyethoxy)phenyl-(2-hydroxy-2-propyl) ketone, 2-benzyl-2-dimethylamino-1-(4-morpholinophenyl) butanone-1,2-hydroxy-2-methyl-1-phenylpropan-1-one, 2-methyl-2-morpholino(4-methylthiophenyl)propan-1-one, and 1-phenyl-1,2-propanedione-2-(o-ethoxycarbonyl)oxime; a benzoin ether-based photopolymerization initiator such as benzoin, benzoin methyl ether, benzoin ethyl ether, benzoin isobutyl ether, and benzoin isopropyl ether; a benzophenone-based photopolymerization initiator, such as benzophenone, 4-hydroxybenzophenone, 2-benzoyl naphthalene, 4-benzoylbiphenyl, 4-benzoyl phenyl ether, acrylated benzophenone, and 1,4-benzoyl benzene; or a thioxanthone-based photopolymerization initiator, such as 2-isopropylthioxanthone, 2-chlorothioxanthone, 2,4-dimethylthioxanthone, 2,4-diethylthioxanthone, and 2,4-dichlorothioxanthone; and the like, but the examples are not limited thereto. Further, examples of other photopolymerization initiators include ethyl anthraquinone, 2,4,6-trimethylbenzoyldiphenyl phosphine oxide, 2,4,6-trimethylbenzoylphenylethoxy phosphine oxide, bis(2,4,6-trimethylbenzoyl)phenyl phosphine oxide, bis(2,4-dimethoxybenzoyl)-2,4,4-trimethylpentyl phosphine oxide, methylphenylglyoxy ester, 9,10-phenanthrene, an acridine-based compound, a triazine-based compound, an imidazole-based compound, and the like, but are not limited thereto. In addition, compounds having photopolymerization promoting effects may be used either alone or in combination with the photopolymerization initiators. Examples of the compounds having photopolymerization promoting effects include triethanolamine, methyldiethanolamine, ethyl 4-dimethylaminobenzoate, isoamyl 4-dimethylaminobenzoate, (2-dimethylamino) ethyl benzoate, 4,4'-dimethylamino benzophenone, and the like, but are not limited thereto.

In an exemplary embodiment of the present specification, the ink composition may further include another additive such as a surfactant. The surfactant is preferably a non-ionic surfactant, and may be a silicone-based or fluorine-based surfactant, but is not limited thereto.

In an exemplary embodiment of the present specification, as a result of measuring the compound represented by Formula 1 by a differential scanning calorimeter (DSC), a difference in temperature between an exothermic peak and an endothermic peak before the exothermic peak is 20° C. or more.

The difference in temperature between the exothermic peak and the endothermic peak before the exothermic peak may be 20° C. to 200° C.

The differential scanning calorimeter (DSC) means a device which can quantitatively measure variables such as a change in enthalpy of a sample to heat based on a quantitative analysis of the sample and a change in area of a peak during the denaturalization of the sample from positions, shapes, and the number of the peaks obtained by showing a flow of heat as a function of temperature from the measurement of an amount of energy (enthalpy) required to maintain the difference in temperature between the sample and a reference material as zero while changing the temperatures of the sample and the reference material at a predetermined rate by a program.

In an exemplary embodiment of the present specification, the ink composition may further include a p-doping material.

In an exemplary embodiment of the present specification, the p-doping material includes $F_4TCNQ$; or a boron anion.

In an exemplary embodiment of the present specification, the p-doping material includes $F_4TCNQ$; or a boron anion, and the boron anion includes a halogen group.

In an exemplary embodiment of the present specification, the p-doping material includes $F_4TCNQ$; or a boron anion, and the boron anion includes F.

In an exemplary embodiment of the present specification, the p-doping material may be selected from the following structures.

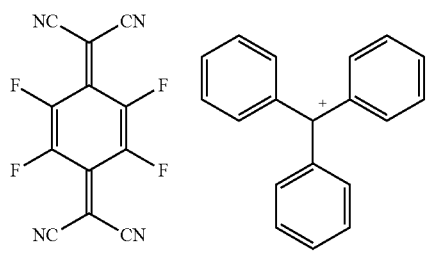

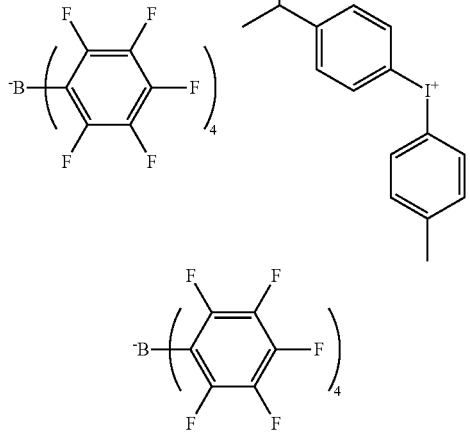

In the present specification, the p-doping material is sufficient as long as the material is a material which allows a host material to have p-semiconductor characteristics, one or two or more thereof may be used, and the type thereof is not limited.

In an exemplary embodiment of the present specification, a content of the p-doping material is preferably 0 wt % to 50 wt %, and more preferably 0 wt % to 30 wt %, based on the compound represented by Formula 1.

The present specification also provides an organic light emitting device formed by using the ink composition.

In an exemplary embodiment of the present specification, the organic light emitting device includes: a first electrode; a second electrode provided to face the first electrode; and an organic material layer having one or more layers provided between the first electrode and the second electrode, in which one or more layers of the organic material layer is formed by using the ink composition.

In an exemplary embodiment of the present specification, the organic material layer formed by using the ink composition is a hole transport layer, a hole injection layer, or a layer which simultaneously transports and injects holes.

In another exemplary embodiment, the organic material layer formed by using the ink composition is a light emitting layer.

In an exemplary embodiment of the present specification, the organic material layer formed by using the ink composition is an electron transport layer or an electron injection layer.

In an exemplary embodiment of the present specification, the organic light emitting device further includes one or two or more layers selected from the group consisting of a hole injection layer, a hole transport layer, an electron transport layer, an electron injection layer, an electron blocking layer, and a hole blocking layer.

In another exemplary embodiment, the organic light emitting device may be an organic light emitting device having a normal type structure in which a second electrode, an organic material layer having one or more layers, and a first electrode are sequentially stacked on a substrate.

In still another exemplary embodiment, the organic light emitting device may be an organic light emitting device having an inverted type structure in which a first electrode, an organic material layer having one or more layers, and a second electrode are sequentially stacked on a substrate.

In an exemplary embodiment of the present specification, the first electrode is a cathode, and the second electrode is an anode.

In an exemplary embodiment of the present specification, the first electrode is an anode, and the second electrode is a cathode.

The organic material layer of the organic light emitting device of the present specification may also be composed of a single-layered structure, but may be composed of a multi-layered structure in which an organic material layer having two or more layers is stacked. For example, the organic light emitting device of the present specification may have a structure including a hole injection layer, a hole transport layer, a light emitting layer, an electron transport layer, an electron injection layer, and the like as organic material layers. However, the structure of the organic light emitting device is not limited thereto, and may include a fewer number of organic layers.

For example, the structure of the organic light emitting device according to an exemplary embodiment of the present specification is exemplified in FIG. 1.

FIG. 1 exemplifies a structure of an organic light emitting device in which an anode 201, a hole injection layer 301, a hole transport layer 401, a light emitting layer 501, an electron transport layer 601, and a cathode 701 are sequentially stacked on a substrate 101.

In an exemplary embodiment of the present specification, the hole injection layer 301 or the hole transport layer 401 in FIG. 1 may be formed by using the ink composition.

In an exemplary embodiment of the present specification, the light emitting layer 501 in FIG. 1 may be formed by using the ink composition.

In an exemplary embodiment of the present specification, the electron transport layer 601 in FIG. 1 may be formed by using the ink composition.

FIG. 1 exemplifies an organic light emitting device, and the organic light emitting device is not limited thereto.

When the organic light emitting device includes a plurality of organic material layers, the organic material layers may be formed of the same material or different materials.

The organic light emitting device of the present specification may be manufactured by the materials and methods known in the art, except that one or more layers of the organic material layer are formed by using the ink composition.

For example, the organic light emitting device of the present specification may be manufactured by sequentially stacking an anode, an organic material layer, and a cathode on a substrate. In this case, the organic light emitting device may be manufactured by depositing a metal or a metal oxide having conductivity, or an alloy thereof on a substrate to form an anode, forming an organic material layer including a hole injection layer, a hole transport layer, a light emitting layer, and an electron transport layer thereon, and then depositing a material, which may be used as a cathode, thereon, by using a physical vapor deposition (PVD) method such as sputtering or e-beam evaporation.

Since the method for manufacturing an organic light emitting device according to an exemplary embodiment of the present specification may form R, G, and B pixels at one time by sequentially jetting R, G, and B inks onto a substrate, in which a bank is formed, through each head to fill the substrate with the inks, and simultaneously drying the substrate, the method has an advantage in that the manufacturing process thereof is much simpler than several deposition processes.

The present specification also provides a method for manufacturing an organic light emitting device formed by using the ink composition.

Specifically, an exemplary embodiment of the present specification provides a method for manufacturing an organic light emitting device, the method including: preparing a substrate; forming a first electrode or a second electron on the substrate; forming an organic material layer having one or more layers on the first electrode or the second electrode; and forming a second electrode or a first electrode on the organic material layer, in which the forming of the organic material layer includes forming an organic material layer having one or more layers by using the ink composition.

According to an exemplary embodiment of the present specification, the organic material layer formed by using the ink composition is formed by using a solution process.

The ink composition according to an exemplary embodiment of the present specification is suitable for a solution process due to the structural characteristics thereof, so that the organic material layer may be formed by a printing method, and as a result, there is an economic effect in terms of time and costs when a device is manufactured.

In another exemplary embodiment of the present specification, examples of the printing method include inkjet printing, nozzle printing, offset printing, transfer printing or screen printing, and the like, but are not limited thereto.

In an exemplary embodiment of the present specification, the organic material layer formed by using the ink composition is formed by using an inkjet printing method.

In an exemplary embodiment of the present specification, the forming an organic material layer having one or more layers by using the ink composition may include subjecting the organic material layer to a heat treatment or a light treatment.

When the forming an organic material layer having one or more layers by using the ink composition includes the subjecting of the organic material layer to the heat treatment or the light treatment, a plurality of photocurable groups or thermosetting groups included in the ink composition may form a cross-linkage, thereby providing an organic material layer including a thin-filmed structure. In this case, it is possible to prevent the organic material layer from being dissolved, morphologically affected or decomposed by a solvent deposited on the surface of the organic material layer formed by using the ink composition.

Therefore, when the organic material layer formed by using the ink composition is formed by a method including the subjecting of the organic material layer to the heat treatment or the light treatment, resistance to a solvent is increased, so that a plurality of layers may be formed by repeatedly carrying out solution deposition and cross-linking methods, and stability is increased, so that service life characteristics of the device may be increased.

In an exemplary embodiment of the present specification, the time for heat-treating the organic material layer formed by using the ink composition is preferably within 1 hour, and more preferably within 30 minutes.

In an exemplary embodiment of the present specification, when the ink composition does not include an additive, it is preferred that a cross-linkage proceeds by performing a heat treatment at a temperature of 100° C. to 250° C., and it is more preferred that a cross-linkage proceeds at a temperature of 120° C. to 200° C. Further, the ink composition of the present specification may further include an initiator, but it is more preferred that the initiator is not used.

In an exemplary embodiment of the present specification, an atmosphere under which the organic material layer formed by using the ink composition is heat-treated is an inert gas such as argon and nitrogen.

In another exemplary embodiment of the present specification, the organic material layer formed by using the ink composition may also be heat-treated under the air atmosphere.

In an exemplary embodiment of the present specification, the ink composition may be mixed with a polymer binding agent and dispersed.

In an exemplary embodiment of the present specification, as the polymer binding agent, those which do not extremely suppress charge transport are preferred, and those which are not strong in absorption to visible light are preferably used. Examples of the polymer binding agent include poly(N-vinylcarbazole), polyaniline, and derivatives thereof, polythiophene and derivatives thereof, poly(p-phenylene vinylene) and derivatives thereof, poly(2,5-thienylene vinylene) and derivatives thereof, polycarbonate, polyacrylate, polymethyl acrylate, polymethyl methacrylate, polystyrene, polyvinyl chloride, polysiloxane, and the like, but are not limited thereto.

As the first electrode material, materials having a high work function are usually preferred so as to facilitate the injection of holes into an organic material layer. Examples thereof include: a metal, such as vanadium, chromium, copper, zinc, and gold, or an alloy thereof; a metal oxide, such as zinc oxide, indium oxide, indium tin oxide (ITO), and indium zinc oxide (IZO); a combination of metal and oxide, such as ZnO:Al or $SnO_2$:Sb; a conductive polymer, such as poly(3-methylthiophene), poly[3,4-(ethylene-1,2-dioxy)thiophene] (PEDOT), polypyrrole, and polyaniline; and the like, but are not limited thereto.

As the second electrode material, materials having a low work function are usually preferred so as to facilitate the injection of electrons into an organic material layer. Examples thereof include: a metal, such as magnesium, calcium, sodium, potassium, titanium, indium, yttrium, lithium, gadolinium, aluminum, silver, tin, and lead, or an alloy thereof; a multi-layered structural material, such as LiF/Al or $LiO_2$/Al; and the like, but are not limited thereto.

The light emitting layer may include a host material and a dopant material. Examples of the host material include a fused aromatic ring derivative, or a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a dibenzofuran derivative, a ladder-type furan compound, a pyrimidine derivative, and the like, but the examples are not limited thereto.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamine group, and examples thereof include pyrene, anthracene, chrysene, periflanthene, and the like having an arylamine group. Further, the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamine group are substituted or unsubstituted. Specific examples thereof include styrylamine, styryl-diamine, styryltriamine, styryltetramine, and the like, but are not limited thereto. Further, examples of the metal complex include an iridium complex, a platinum complex, and the like, but are not limited thereto.

In the present specification, when the organic material layer formed by the ink composition is not a light emitting layer or an additional light emitting layer is provided, a light emitting material of the light emitting layer is a material which may emit light in a visible light region by accepting and combining holes and electrons from a hole transport layer and an electron transport layer, respectively, and preferably a material having high quantum efficiency for fluorescence or phosphorescence. Examples thereof include: an 8-hydroxy-quinoline aluminum complex (Alq3); a carbazole-based compound; a dimerized styryl compound; BAlq; a 10-hydroxybenzoquinoline-metal compound; benzoxazole-based, benzothiazole-based and benzimidazole-based compounds; a poly(p-phenylenevinylene) (PPV)-based polymer; a spiro compound; polyfluorene; lubrene; and the like, but are not limited thereto.

The hole injection layer is a layer which injects holes from an electrode. A hole injection material has an ability to transport holes, so that it is preferred that the hole injection material has a hole injection effect in a first electrode and an excellent hole injection effect for a light emitting layer or a light emitting material. Further, the hole injection material is preferably a material which is excellent in ability to prevent excitons produced from a light emitting layer from moving to an electron injection layer or an electron injection material. In addition, the hole injection material is preferably a material which is excellent in ability to form a thin film. Furthermore, the highest occupied molecular orbital (HOMO) of the hole injection material is preferably a value between the work function of the second electrode material and the HOMO of the neighboring organic material layer. Specific examples of the hole injection material include: metal porphyrin, oligothiophene, and arylamine-based organic materials; hexanitrile hexaazatriphenylene-based organic materials; quinacridone-based organic materials; perylene-based organic materials; polythiophene-based conductive polymers such as anthraquinone and polyaniline; and the like, but are not limited thereto.

The hole transport layer is a layer which accepts holes from a hole injection layer and transports the holes to a light emitting layer. A hole transport material is preferably a material having high hole mobility which may receive holes transported from a first electrode or a hole injection layer and transfer the holes to a light emitting layer. Specific examples thereof include an arylamine-based organic material, a conductive polymer, a block copolymer having both conjugated portions and non-conjugated portions, and the like, but are not limited thereto.

The electron transport layer is a layer which accepts electrons from an electron injection layer and transports the electrons to a light emitting layer. An electron transport material is preferably a material having high electron mobility which may proficiently receive electrons from a second electrode and transfer the electrons to a light emitting layer. Specific examples thereof include: an Al complex of 8-hydroxyquinoline; a complex including Alq3; an organic radical compound; a hydroxyflavone-metal complex; and the like, but are not limited thereto. The electron transport layer may be used with any desired first electrode material, as used according to the related art. In particular, appropriate examples of the first electrode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode. It is preferred that an electron injection material is excellent in ability to transport electrons and has an electron injection effect from the second electrode and an excellent electron injection effect for a light emitting layer or a light emitting material. Further, the electron injection material is preferably a material which prevents excitons produced from a light emitting layer from moving to a hole injection layer and is excellent in ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, metal complex compounds, nitrogen-containing 5-membered ring derivatives, and the like, but are not limited thereto.

Examples of the metal complex compounds include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris (2-methyl-8-hydroxyquinolinato) aluminum, tris(8-hydroxyquinolinato) gallium, bis(10-hydroxybenzo[h] quinolinato) beryllium, bis(10-hydroxybenzo[h] quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The electron blocking layer is a layer which may improve the service life and efficiency of a device by preventing holes injected from a hole injection layer from passing through a light emitting layer and entering an electron injection layer. The publicly-known material can be used without limitation, and may be formed between a light emitting layer and a hole injection layer, or between a light emitting layer and a layer which simultaneously injects and transports holes.

The hole blocking layer is a layer which blocks holes from reaching a second electrode, and may be generally formed under the same conditions as those of the hole injection layer. Specific examples thereof include an oxadiazole derivative or a triazole derivative, a phenanthroline derivative, an aluminum complex, and the like, but are not limited thereto.

The organic light emitting device according to the present specification may be a top emission type, a bottom emission type, or a dual emission type according to the materials to be used.

MODE FOR INVENTION

Hereinafter, the present specification will be described in detail with reference to Examples for specifically describing the present specification. However, the Examples according to the present specification may be modified in various forms, and it is not interpreted that the scope of the present specification is limited to the Examples described below. The Examples of the present specification are provided to more completely explain the present specification to a person with ordinary skill in the art.

PREPARATION EXAMPLES

<Preparation Example 1> Preparation of Compound 1-1

(1) Synthesis of Intermediate 3

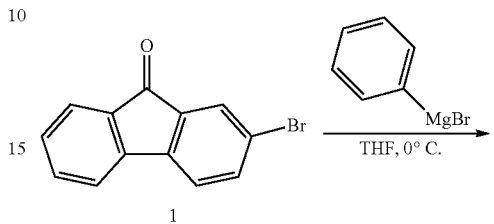

1

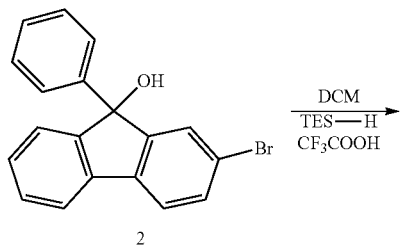

2

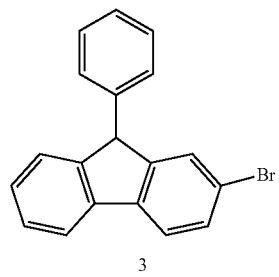

3

After 2-bromo-9H-fluoren-9-one (5 g, 19.3 mmol) was dissolved in anhydrous tetrahydrofuran [THF], a flask containing the solution was put into an ice water bath. Phenylmagnesiumbromide (3 M in tetrahydrofuran [THF], 9.65 ml, 29.0 mmol) was added thereto, and the resulting mixture was stirred at 0° C. for 20 minutes. The reaction was stopped with $NH_4Cl$ (aq), and the product was extracted with diethyl ether ($Et_2O$). The organic layer was dried using $MgSO_4$, and the organic solvent was removed using a vacuum rotary concentrator. The residue was column purified to obtain 6.5 g (quantitative yield) of Intermediate 2.

After Intermediate 2 (3.6 g, 10.6 mmol) was dissolved in dichloromethane [DCM], triethylsilane (2.6 ml, 16.1 mmol) and 1.3 ml of trifluoroacetic acid were added thereto, and the resulting mixture was stirred at room temperature overnight. After it was confirmed by thin layer chromatography (TLC) that Intermediate 2 did not remain, silica gel was added thereto, and the organic solvent was removed by a vacuum rotary concentrator. A silica gel onto which the product was adsorbed was column purified to obtain 3.26 g (yield 95%) of Intermediate 3.

(2) Synthesis of Intermediate 5

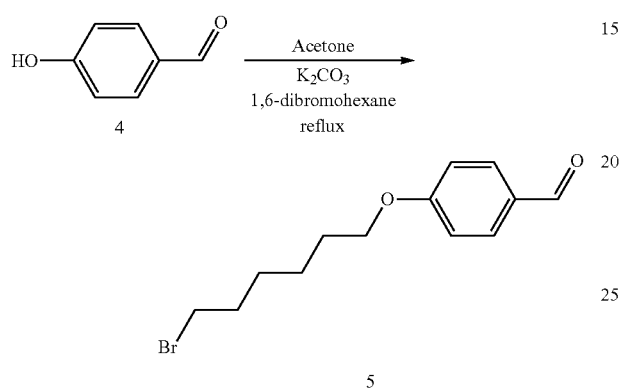

After 4-hydroxybenzaldehyde (6.1 g, 50 mmol), potassium carbonate (10 g, 75 mmol), and 1,6-dibromohexane (15 ml, 100 mmol) were dissolved in acetone, the resulting solution was refluxed for 3 hours. After the reactant was filtered, the organic solvent was removed using a vacuum rotary concentrator. The residue was column purified to obtain 9.9 g (yield 69%) of Intermediate 5.

(3) Synthesis of Intermediate 7

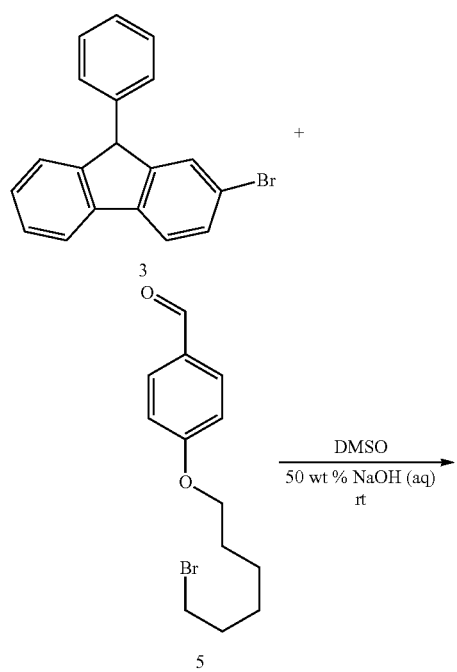

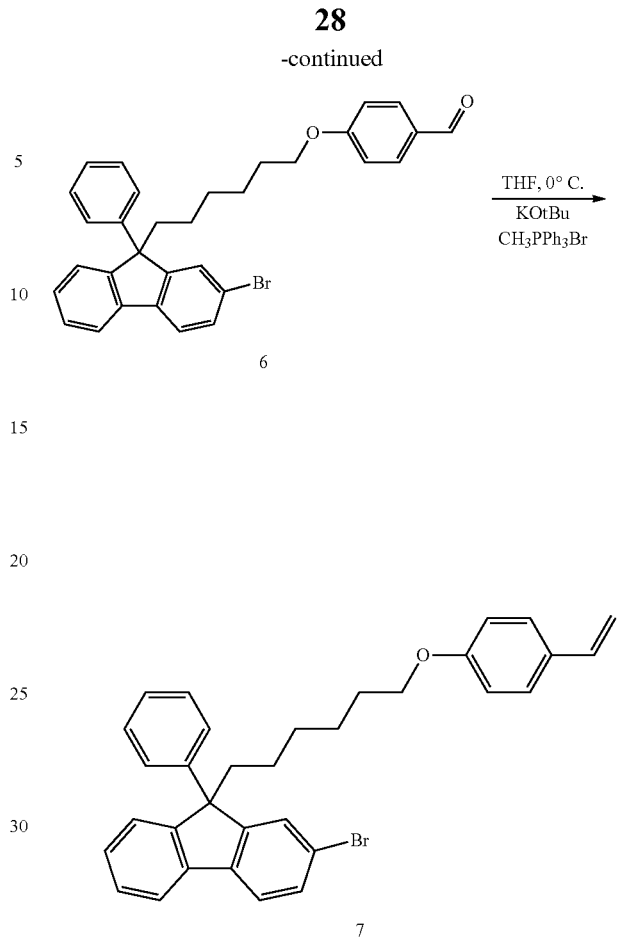

Intermediate 3 (3.7 g, 11.5 mmol) and Intermediate 5 (3 g, 10.5 mmol) were dissolved in 20 ml of dimethyl sulfoxide [DMSO] in an oil bath at 50° C. After 0.5 ml of 50 wt % NaOH (aq) was added thereto and the resulting mixture was stirred overnight, 0.5 ml of 50 wt % NaOH (aq) was added again thereto, and the resulting mixture was further stirred for 2 hours. The reactant was added to 400 ml of water and precipitated, and then the precipitate was filtered. A solid obtained by filtration was added again to 100 ml of ethanol, the resulting mixture was stirred for 10 minutes, and then the product was filtered again. The filter cake was dried in a vacuum oven to obtain 4.48 g (yield 81%) of Intermediate 6.

After a flask containing methyl phosphonium bromide (5.1 g, 14.3 mmol) was put into ice water, 100 ml of anhydrous tetrahydrofuran [THF] was added thereto. KOtBu (1.6 g, 14.3 mmol) was added thereto, and the resulting mixture was stirred for 30 minutes. 4-((6-(2-bromo-9-phenyl-9H-fluoren-9-yl)hexyl)oxy)benzaldehyde (3 g, 5.7 mmol) was dissolved in anhydrous tetrahydrofuran [THF], and the resulting solution was put into a reaction flask and stirred again for 1 hour. After the reaction was stopped by adding water thereto, the product was extracted with dichloromethane [DCM]. After the organic solvent was dried over MgSO$_4$ and filtered, the organic solvent was removed using a vacuum rotary concentrator. The residue was column purified to obtain 2.63 g (yield 88%) of Intermediate 7.

(4) Synthesis of Compound 1-1

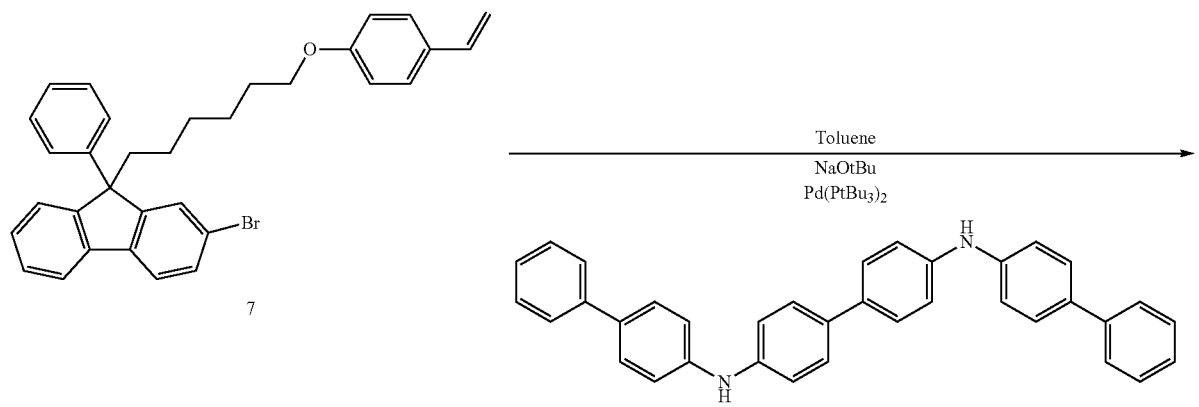

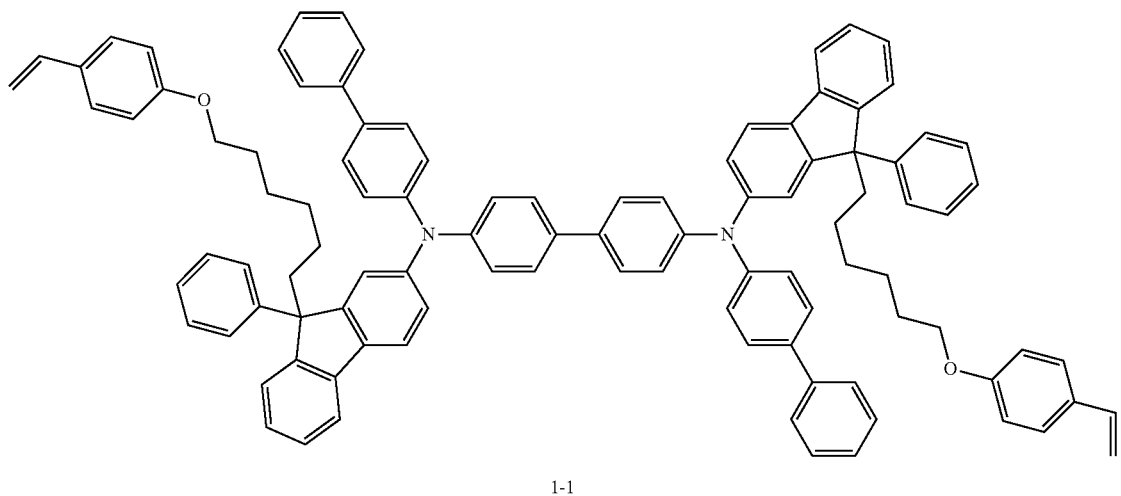

Intermediate 7 (700 mg, 1.34 mmol), N4,N4'-di([1,1'-biphenyl]-4-yl)-[1,1'-biphenyl]-4,4'-diamine (327 mg, 0.67 mmol), and NaOtBu (384 mg, 4 mmol) were put into a 50-ml round flask, and 7 ml of anhydrous toluene was added thereto. After the round flask containing the reactant was put into an oil bath at 90° C. and the reactant was stirred for 4 hours, the oil bath was removed, and the product was diluted with dichloromethane [DCM]. Silica gel and celite were added thereto, and the resulting mixture was stirred for 5 minutes and then filtered. After the organic solvent was removed from the filtrate by using a vacuum rotary concentrator, the residue was column purified to obtain 560 mg (yield 61%, HPLC purity 99.4%) of Compound 1-1.

NMR measurement value of Compound 1-1: $^1$H NMR (500 MHz, CD$_2$Cl$_2$) δ 7.70 (d, 2H), 7.68 (d, 2H), 7.57 (d, 4H), 7.48 (t, 8H), 7.41 (t, 4H), 7.34-7.26 (m, 8H), 7.23-7.10 (m, 26H), 6.76 (d, 4H), 6.64-6.58 (dd, 2H), 5.56 (d, 2H), 5.07 (d, 2H), 3.85 (t, 4H), 2.46-2.36 (m, 4H), 1.67-1.61 (m, 4H) 1.35-1.23 (m, 8H), 0.92-0.73 (m, 4H)

<Preparation Example 2> Preparation of Compound 1-2

(1) Synthesis of Intermediate 10

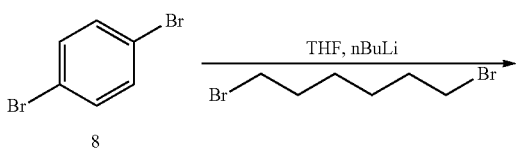

(2) Synthesis of Intermediate 11

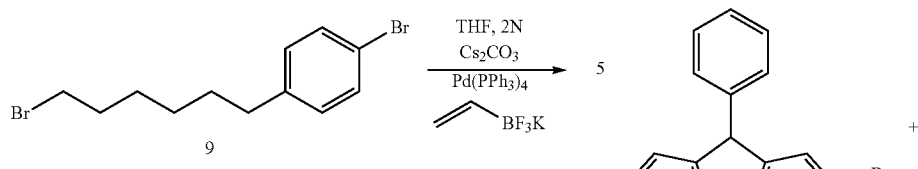

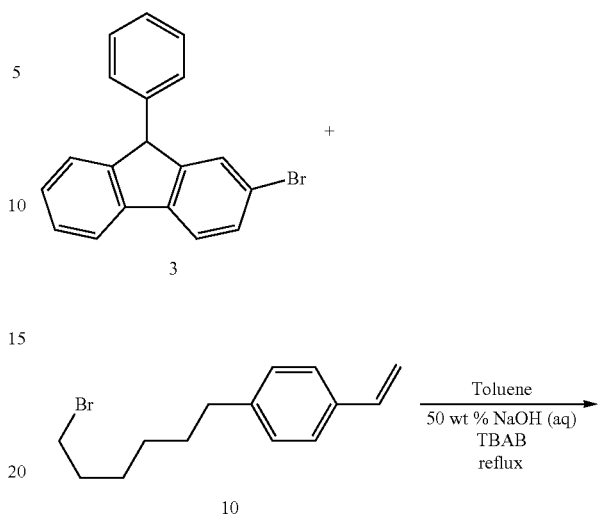

After 1,4-dibromobenzene (8.0 g, 33.9 mmol) was dissolved in tetrahydrofuran [THF], the temperature was lowered by using a dry ice/acetone bath. After nBuLi (13.6 ml, 33.9 mmol, 2.5 M in hexane) was slowly added thereto, the resulting mixture was stirred for 1 hour. Thereafter, 1,6-dibromohexane (11 ml, 72 mmol) was added thereto, and then the resulting mixture was stirred overnight. After the reaction was stopped with water, the product was extracted with dichloromethane. The extract was subjected to distillation purification to obtain 5.7 g (yield 53%) of Intermediate 9.

After Intermediate 9 (3.0 g, 9.4 mmol) and a vinyl trifluoroborane potassium salt (1.9 g, 14 mmol) were dissolved in tetrahydrofuran [THF], a 2N aqueous $Cs_2CO_3$ solution and $Pd(PPh_3)_4$ (1.1 mg, 0.94 mmol) were added thereto, and the resulting mixture was stirred under the reflux conditions for 6 hours. Thereafter, water was added thereto, and the product was extracted with ethyl acetate. The organic layer was dried over $MgSO_4$, and the residue was concentrated by using a vacuum rotary concentrator, and then column purified to obtain 2.06 g (yield 82%) of Intermediate 10.

Intermediate 10 (532 mg, 2.0 mmol) and Intermediate 3 (642 mg, 2.0 mmol) were dissolved in 20 ml of toluene, 4.5 ml of 50 wt % NaOH was added thereto, and then the resulting mixture was stirred under reflux for 12 hours. The product was extracted with dichloromethane and dried over $MgSO_4$. The extract was concentrated using a vacuum rotary concentrator, and then column purified to obtain 788 mg (yield 78%) of Intermediate 11.

(3) Synthesis of Compound 1-2

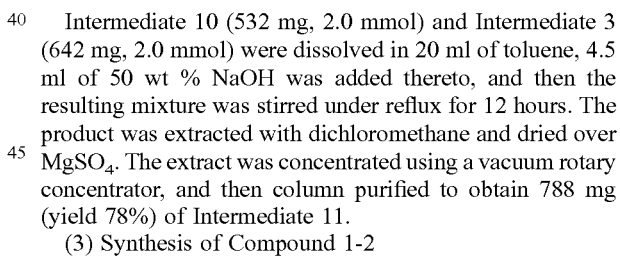

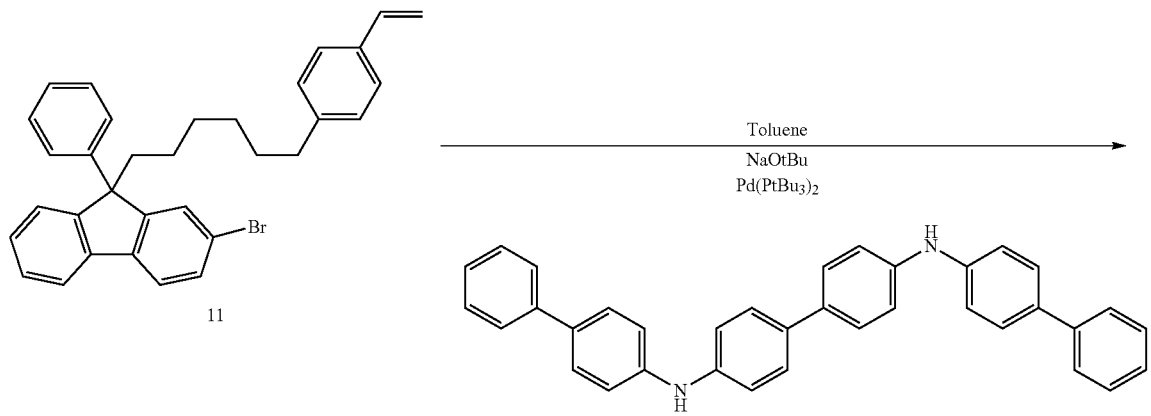

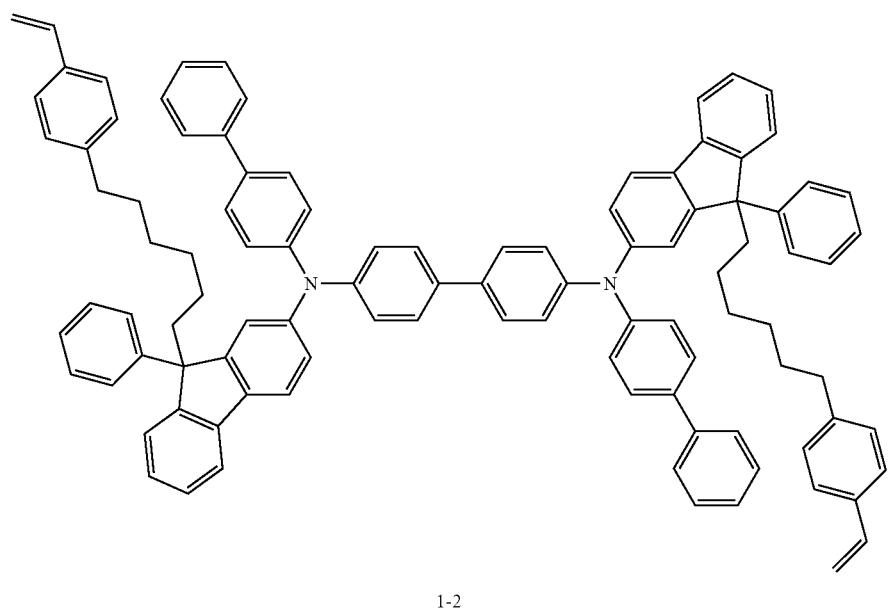

1-2

After Intermediate 11 (788 mg, 1.56 mmol), N4,N4'-di ([1,1'-biphenyl]-4-yl)-[1,1'-biphenyl]-4,4'-diamine (362 mg, 0.74 mmol), and NaOtBu (427 mg, 4.4 mmol) were put into a 50-ml round flask, 13 ml of anhydrous toluene was added thereto. After the round flask containing the reactant was put into an oil bath at 80° C. and the reactant was stirred for 4 hours, the oil bath was removed, and the product was diluted with dichloromethane [DCM]. Silica gel and celite were added thereto, and the resulting mixture was stirred for 5 minutes and then filtered. After the organic solvent was removed from the filtrate by using a vacuum rotary concentrator, the residue was column purified to obtain 634 mg (yield 64%, HPLC purity 99.2%) of Compound 1-2.

NMR measurement value of Compound 1-2: $^1$H NMR (500 MHz, CD$_2$Cl$_2$) δ 7.70-7.68 (m, 4H), 7.57 (d, 4H), 7.47 (t, 8H), 7.42 (t, 4H), 7.34-7.29 (m, 4H), 7.26 (d, 4H), 7.22-7.12 (m, 26H), 7.05 (d, 4H), 6.67-6.61 (dd, 2H), 5.64 (d, 2H), 5.13 (d, 2H), 2.49 (t, 4H), 2.42-2.34 (m, 4H), 1.50-1.44 (m, 4H), 1.26-1.10 (m, 8H), 0.90-0.81 (m 4H)

<Preparation Example 3> Preparation of Compound 1-3

(1) Synthesis of Intermediate 22

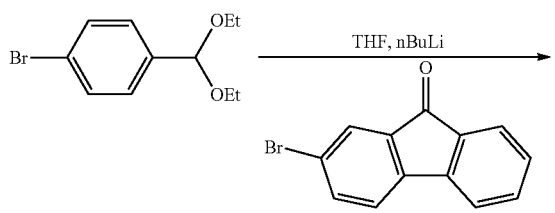

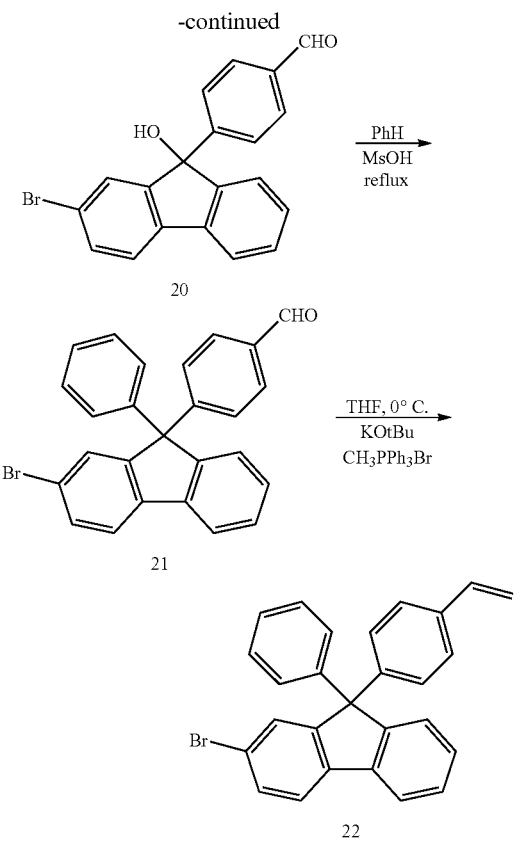

After 1-bromo-4-(diethyoxymethyl)benzene (13.2 ml, 64.9 mmol) was dissolved in tetrahydrofuran [THF], the temperature was lowered to −78° C. nBuLi (2.5 M in hexane, 24 ml, 60 mmol) was added thereto, and the resulting mixture was stirred at −78° C. for 30 minutes. 2-bromo-9H-fluoren-9-one (10 g, 38.6 mmol) was added thereto at one time and the resulting mixture was stirred overnight. The reaction was terminated with 1 N HCl (aq), followed by extraction with ethyl acetate. After the extract was dried by using magnesium sulfate (MgSO$_4$) and filtered, the organic solvent was removed by a vacuum rotary concentrator. After the residue was column purified, the purified product was recrystallized (toluene/hexane) to obtain 13 g (yield 55%) g of Intermediate 20.

After 140 ml of benzene was put into Intermediate 20 (4.5 g, 12.3 mmol) and methane sulfonic acid (400 μl, 6.16 mmol) was added thereto, the resulting mixture was refluxed by using a dean-stark apparatus. The acid was neutralized with saturated NaHCO$_3$(aq), followed by column purification to obtain 2.73 g (yield 52%) of Intermediate 21.

Intermediate 21 (2.9 g, 6.82 mmol) and CH$_3$BrPPh$_3$ (4.89 g, 13.7 mmol) were put into tetrahydrofuran [THF], potassium tert-butoxide (1.553 g, 13.7 mmol) was added thereto at 0° C., and the resulting mixture was stirred for 1 hour. The reaction was stopped with water, and the product was extracted with ethyl acetate. After the extract was dried by putting magnesium sulfate (MgSO$_4$) thereinto and filtered, the organic solvent was removed by a vacuum rotary concentrator. The residue was column purified to obtain 2.8 g (yield 97%) of Intermediate 22.

(2) Synthesis of Compound 1-3

Toluene was put into a flask containing Intermediate (1.58 g, 3.74 mmol), N4,N4y-diphenyl-[1,1'-biphenyl]-4,4'-diamine (572 mg, 1.7 mmol) and sodium tert-butoxide (980 mg, 10.2 mmol), and the flask was bubbled with nitrogen. The flask was put into an oil bath at 90° C., and then Pd(PtBu$_3$)$_2$ (43 mg, 0.085 mmol) was added thereto, and the resulting mixture was stirred for 24 hours. The reaction was stopped by adding water thereto, the product was extracted with dichloromethane (DCM), and then the organic layer was dried over MgSO$_4$. After the organic solvent was removed using a vacuum rotary concentrator, the residue was column purified to obtain 950 mg (yield 55%) of Compound 1-3.

NMR measurement value of Compound 1-3: $^1$H NMR (500 MHz, CD$_2$Cl$_2$) δ 7.71 (d, 2H), 7.65 (d, 2H), 7.42 (d, 4H), 7.35 (d, 4H), 7.27-7.20 (m, 18H), 7.17-7.13 (m, 4H), 7.11-7.06 (m, 14H), 7.03 (t, 2H), 6.70-6.64 (dd, 2H), 5.69 (d, 2H), 5.19 (d, 2H)

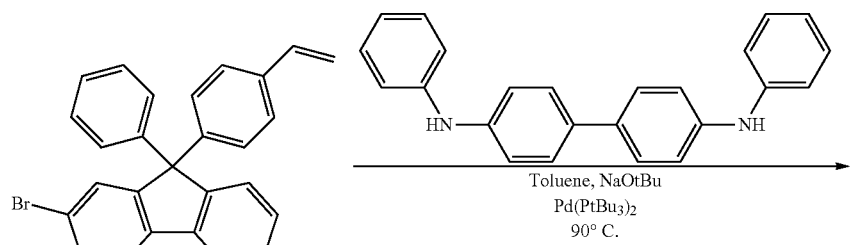

22

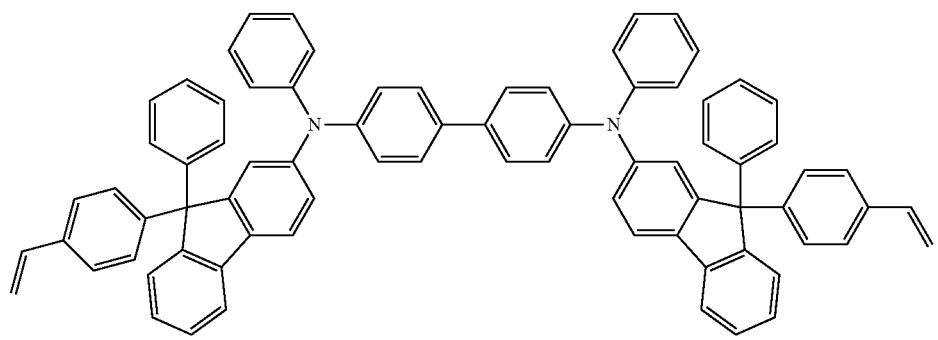

1-3

<Preparation Example 4> Preparation of Compound 1-4

(1) Synthesis of Intermediate 24

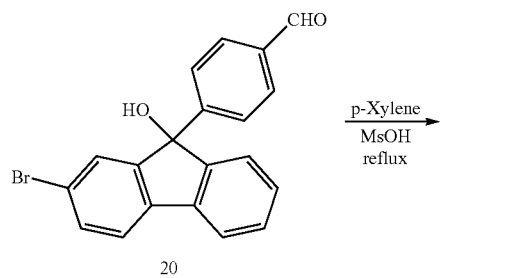

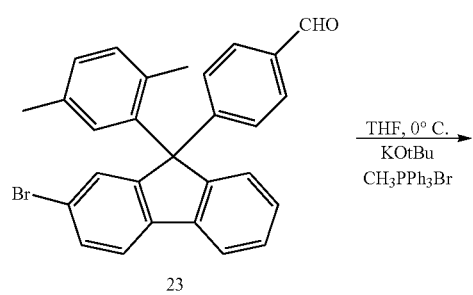

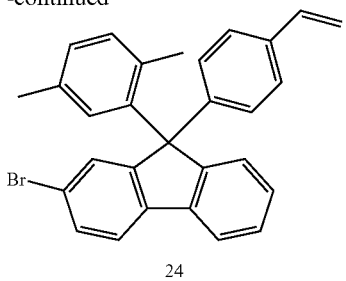

140 ml of p-xylene was put into Intermediate 20 (5.11 g, 14 mmol), methane sulfonic acid (1.8 ml, 28 mmol) was added thereto, and then the resulting mixture was stirred at 70° C. for 24 hours. The acid was neutralized with saturated $NaHCO_3$(aq), followed by extraction with ethyl acetate. After the extract was dried over magnesium sulfate ($MgSO_4$) and filtered, the organic solvent was removed by a vacuum rotary concentrator. The residue was column purified to obtain 4.3 g (yield 68%) of Intermediate 23.

100 ml of anhydrous THF was put into $CH_3BrPPh_3$ (11.8 g, 33.19 mmol), potassium tert-butoxide (3.2 g, 28.44 mmol) was added thereto at 0° C., and the resulting mixture was stirred for 10 minutes. Intermediate 23 (4.3 g, 9.48 mmol) was dissolved in anhydrous THF (20 ml, 10 ml, 10 ml), the resulting solution was added thereto, and 10 minutes later, the reaction was stopped with water, and the product was extracted with ethyl acetate. After the extract was dried over $NaSO_4$ and filtered, the organic solvent was removed by a vacuum rotary concentrator. The residue was column purified to obtain 3.88 g (yield 91%) of Intermediate 24.

(2) Synthesis of Compound 1-4

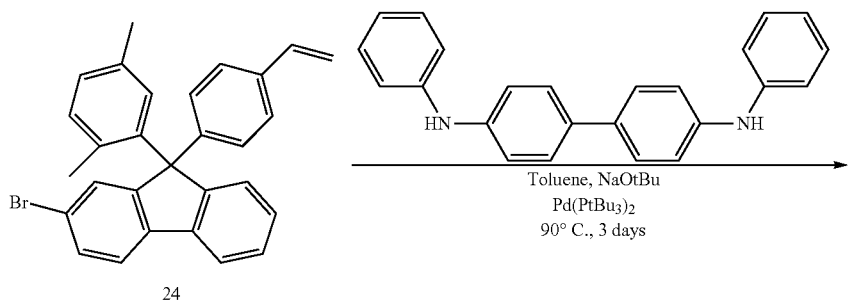

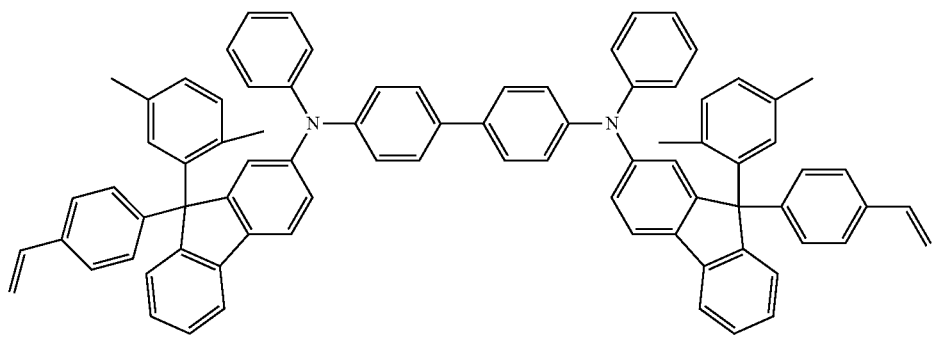

Toluene was put into a flask containing Intermediate (1.37 g, 3.03 mmol), N4,N4'-diphenyl-[1,1'-biphenyl]-4,4'-diamine (464 mg, 1.38 mmol) and sodium tert-butoxide (769 mg, 8.3 mmol), and the flask was bubbled with nitrogen. The flask was put into an oil bath at 90° C., and then Pd(PtBu$_3$)$_2$ (36 mg, 0.085 mmol) was added thereto, and the resulting mixture was stirred for 24 hours. The reaction was stopped by adding water thereto, the product was extracted with dichloromethane (DCM), and then the organic layer was dried over MgSO$_4$. After the organic solvent was removed using a vacuum rotary concentrator, the residue was column purified to obtain 500 mg (yield 34%) of Compound 1-4.

NMR measurement value of Compound 1-4: $^1$H NMR (500 MHz, CD$_2$Cl$_2$) δ 7.70 (d, 2H), 7.63 (d, 2H), 7.43 (d, 4H), 7.37 (t, 2H), 7.30-7.20 (m, 14H), 7.15-7.05 (m, 14H), 7.02 (t, 2H), 6.93 (s, 4H), 6.86 (s, 2H), 6.71-6.65 (dd, 2H), 5.70 (d, 2H), 5.20 (d, 2H), 2.15 (s, 6H), 1.57 (s, 6H)

<Preparation Example 5> Preparation of Compound 1-5

Toluene was put into a flask containing Intermediate (1.53 g, 3.61 mmol), N4,N4'-di(biphenyl-4-yl)biphenyl-4,4'-diamine (801 mg, 1.64 mmol) and sodium tert-butoxide (946 mg, 9.84 mmol), and the flask was bubbled with nitrogen. The flask was put into an oil bath at 90° C., and then Pd(PtBu$_3$)$_2$ (42 mg, 0.08 mmol) was added thereto, and the resulting mixture was stirred for 24 hours. The reaction was stopped by adding water thereto, the product was extracted with dichloromethane (DCM), and then the organic layer was dried over MgSO$_4$. After the organic solvent was removed using a vacuum rotary concentrator, the residue was column purified to obtain 1.06 mg (yield 55%, HPLC purity 99.4%) of Compound 1-5.

NMR measurement value of Compound 1-5: $^1$H NMR (500 MHz, CD$_2$Cl$_2$) δ 7.73 (d, 2H), 7.69 (d, 2H), 7.59 (d, 4H), 7.48 (t, 8H), 7.43 (t, 4H), 7.38-7.30 (m, 8H), 7.28-7.11 (m, 30H), 6.71-6.65 (dd, 2H), 5.69 (d, 2H), 5.20 (d, 2H)

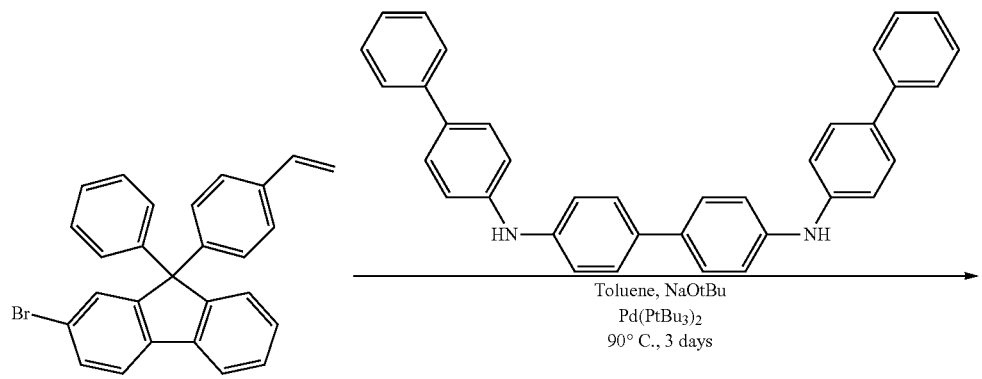

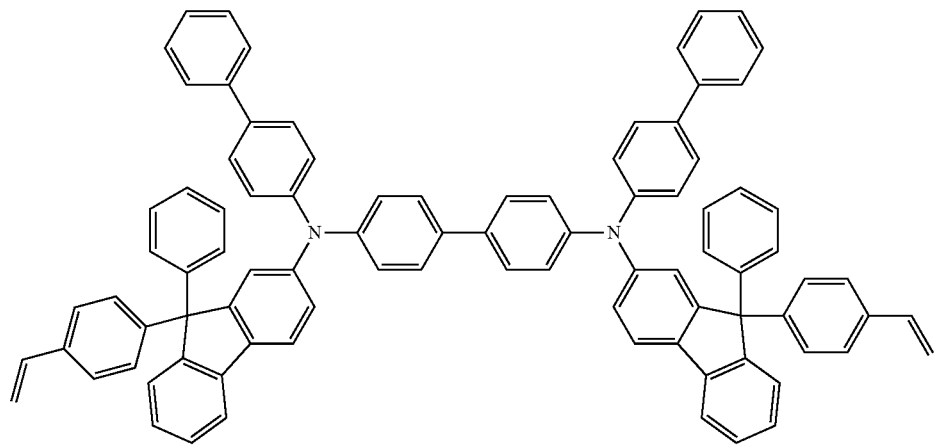

1-5

<Preparation Example 6> Preparation of Compound 1-6

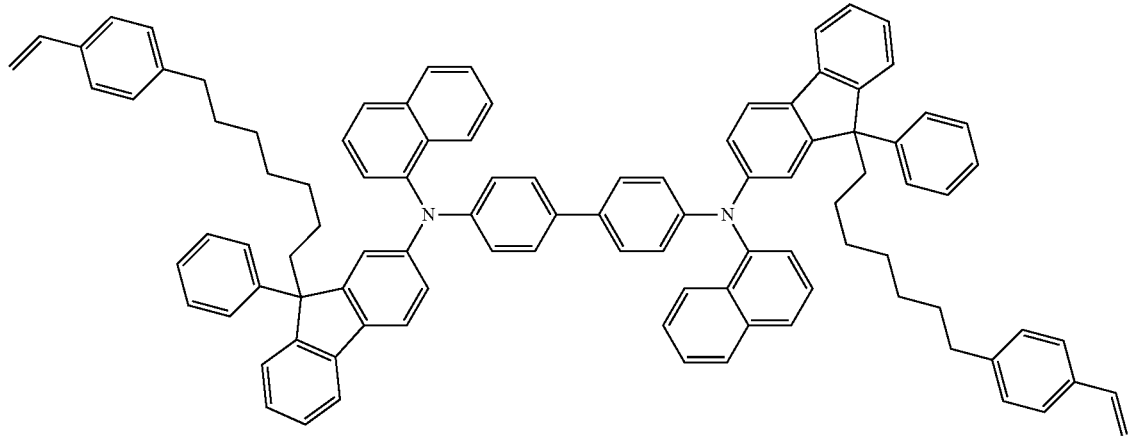

579 mg (yield 60%) of Compound 1-6 was obtained by performing the experiment in the same manner as in Preparation Example 2, except that in Preparation Example 2, 1,7-dibromoheptane and N4,N4'-di(naphthalen-1-yl)biphenyl-4,4'-diamine were used instead of 1,6-dibromohexane] and N4,N4'-di(biphenyl-4-yl)biphenyl-4,4'-diamine, respectively.

Example 1

40 mg of Compound 1-1 prepared above was dissolved at a concentration of 2 wt % in 1.96 g of a solvent (Compound 2-1 [p-tolyl n-octanoate]) to prepare an ink composition.

Examples 2 to 22 and Comparative Examples 1 to 18

The ink compositions in Examples 2 to 22 and Comparative Examples 1 to 18 were prepared in the same manner as in Example 1, except that the functional layer materials and the solvents were used as in the following Tables 1 to 6. As the solvents used in the following Tables 1 to 6, products manufactured by Tokyo Chemical Industry (TCI) Co., Ltd. and Aldrich Chemical Company, Inc. were used. Examples 2, 3, 7, 10, 11, 14, 17, 18, 20, and 21 include the solvent represented by Formula 2 and a subsolvent as solvents, and the numerical value in the parenthesis means a weight ratio of the solvent of Formula 2 to the subsolvent.

EVALUATION EXAMPLES

<Evaluation Example 1>—Evaluation of Solubility

The solubilities of the ink compositions prepared in Examples 1 to 22 and Comparative Examples 1 to 18 at 25° C. and 1 atm were measured and evaluated with the following criteria, and the results thereof are shown in the following Tables 1 to 6.
  2.0 wt % or more: Excellent
  0.5 wt % or more and less than 2.0 wt %: Good
  Less than 0.5 wt %: Poor <Evaluation Example 2>—Evaluation of Discharge Stability The discharge stability was measured by using a Fujifilm, Dimatix DMP-2800 apparatus, 10 pl cartridge (DMC-11610) and evaluated with the following criteria, and the results thereof are shown in the following Tables 1 to 6. A case where the solubility was not good and the discharge stability could not be evaluated was marked with "-".
  The ink composition is stably and linearly discharged while all the nozzles are not clogged for 5 minutes or more: O.K.
  The case where the ink composition is not discharged or ink drops are distorted during the discharge of the ink composition: N.G.

<Evaluation Example 3>—Evaluation of Image of Film

After each of the ink compositions prepared in Examples 1 to 22 and Comparative Examples 1 to 18 was jetted onto an ITO substrate in which a bank was formed, the ITO substrate was dried under vacuum ($10^{-6}$ torr) for 15 minutes. After a heat treatment was performed on a hot plate at 220° C. for 30 minutes, it was observed by an optical microscope whether the film was formed well. The film was evaluated with the following criteria, and the results thereof are shown in the following Tables 1 to 6. A case where the solubility was not good and the image of the film could not be evaluated was marked with "-".
  Impurities such as grains, bright spots, white spots, and the like are not observed in a pixel: O.K.
  Impurities such as grains, bright spots, white spots, and the like are observed in a pixel: N.G.

<Evaluation Example 4>—Evaluation of Flatness of FILM

After each of the ink compositions prepared in Examples 1 to 22 and Comparative Examples 1 to 18 was jetted onto an ITO substrate in which a bank was formed, the ITO substrate was dried under vacuum (10$^{-6}$ torr) for 15 minutes. After a heat treatment was performed on a hot plate at 220° C. for 30 minutes, it was observed by an optical microscope whether the film was formed well. The thickness of the film was measured by using an optical profiler (OP), the flatness of the film was evaluated with the following criteria, and the results thereof are shown in the following Tables 1 to 6. A case where the solubility was not good and the flatness of the film could not be evaluated was marked with "-".

Flatness is less than 0.25: O.K.
Flatness is 0.25 or more: N.G.

The flatness was calculated by using the following equation.

$$\text{Flatness} = \frac{|H_{90} - Hc|}{Hc} \quad \text{[Equation]}$$

Hc means the height of the center of the ink layer as in FIG. 2, and H$_{90}$ means the height at the 90% position of the ink layer as follows. That is, when the length of the x-axis of the pixel is 100 in total, Hc means the height at the position of 50, and H$_{90}$ means the height at the position of 5 or 95.

TABLE 1

|  | Functional layer material | Solvent | Solubility | Film image | Discharge stability | Film flatness measurement value (x axis/y axis) | Film flatness |
|---|---|---|---|---|---|---|---|
| Example 1 | Compound 1-1 | Compound 2-1 | Excellent | O.K | O.K | 0.007/0.004 | O.K |
| Example 2 | Compound 1-1 | Compound 2-1 + 3-ethylbiphenyl (7:3) | Excellent | O.K | O.K | 0.05/0.21 | O.K |
| Example 3 | Compound 1-1 | Compound 2-1 + 2-Isopropyl naphthalene (3:7) | Excellent | O.K | O.K | 0.03/0.06 | O.K |
| Example 4 | Compound 1-1 | Compound 2-2 | Excellent | O.K | O.K | 0.02/0.04 | O.K |
| Example 5 | Compound 1-1 | Compound 2-7 | Excellent | O.K | O.K | 0.015/0.07 | O.K |
| Comparative Example 1 | Compound 1-1 | 1-ethylnaphthalene | Excellent | O.K | O.K | 0.23/0.80 | N.G |
| Comparative Example 2 | Compound 1-1 | Benzyl ether | Excellent | N.G | O.K | — | N.G |
| Comparative Example 3 | Compound 1-1 | Ethyl decanoate | Poor | — | — | — | — |
| Comparative Example 4 | Compound 1-1 | Isoamyl benzoate | Excellent | O.K | O.K | 0.12/0.33 | N.G |
| Comparative Example 13 | Compound 1-1 | Benzyl acetate | Excellent | O.K. | N.G | 0.04/0.42 | N.G. |
| Comparative Example 14 | Compound 1-1 | o-tolyl acetate | Excellent | O.K. | N.G | 0.11/0.20 | N.G. |

TABLE 2

|  | Functional layer material | Solvent | Solubility | Film image | Discharge stability | Film flatness measurement value (x axis/y axis) | Film flatness |
|---|---|---|---|---|---|---|---|
| Example 6 | Compound 1-2 | Compound 2- | Excellent | O.K | O.K | 0.002/0.037 | O.K |
| Example 7 | Compound 1-2 | Compound 2-1 + 2-phenylethylalcohol (5:5) | Excellent | O.K | O.K | 0.02/0.01 | O.K |
| Example 8 | Compound 1-2 | Compound 2-7 | Excellent | O.K | O.K | 0.02/0.05 | O.K |
| Comparative Example 5 | Compound 1-2 | Dimethyl phthalate | Excellent | O.K | O.K | 0.12/0.97 | N.G |
| Comparative Example 6 | Compound 1-2 | Benzyl ether | Excellent | N.G | O.K | — | N.G |
| Comparative Example 7 | Compound 1-2 | Ethyl decanoate | Poor | — | — | — | — |
| Comparative Example 15 | Compound 1-2 | o-tolyl acetate | Excellent | O.K. | N.G | 0.08/0.31 | N.G. |

TABLE 3

| | Functional layer material | Solvent | Solubility | Film image | Discharge stability | Film flatness measurement value (x axis/y axis) | Film flatness |
|---|---|---|---|---|---|---|---|
| Example 9 | Compound 1-3 | Compound 2-1 | Excellent | O.K | O.K | 0.004/0.009 | O.K |
| Example 10 | Compound 1-3 | Compound 2-1 + 3-ethylbiphenyl (7:3) | Excellent | O.K | O.K | 0.02/0.18 | O.K |
| Example 11 | Compound 1-3 | Compound 2-1 + 2-Isopropyl naphthalene (3:7) | Excellent | O.K | O.K | 0.07/0.22 | O.K |
| Example 12 | Compound 1-3 | Compound 2-2 | Excellent | O.K | O.K | 0.05/0.13 | O.K |
| Comparative Example 8 | Compound 1-3 | amyl benzoate | Excellent | O.K | O.K | 0.3/0.95 | N.G |
| Comparative Example 9 | Compound 1-3 | Ethyl decanoate | Poor | — | N.G | — | — |
| Comparative Example 16 | Compound 1-3 | Benzyl acetate | Excellent | O.K. | N.G | 0.02/0.37 | N.G. |

TABLE 4

| | Functional layer material | Solvent | Solubility | Film image | Discharge stability | Film flatness measurement value (x axis/y axis) | Film flatness |
|---|---|---|---|---|---|---|---|
| Example 13 | Compound 1-4 | Compound 2-1 | Excellent | O.K | O.K | 0.018/0.01 | O.K |
| Example 14 | Compound 1-4 | Compound 2-1 + 2-Isopropyl naphthalene (3:7) | Excellent | O.K | O.K | 0.08/0.16 | O.K |
| Example 15 | Compound 1-4 | Compound 2-2 | Excellent | O.K | O.K | 0.05/0.20 | O.K |
| Comparative Example 10 | Compound 1-4 | 1-ethylnaphthalene | Good | O.K | O.K | 0.14/0.28 | N.G |
| Comparative Example 17 | Compound 1-4 | Benzyl acetate | Excellent | O.K. | N.G | 0.11/0.33 | N.G. |

TABLE 5

| | Functional layer material | Solvent | Solubility | Film image | Discharge stability | Film flatness measurement value (x axis/y axis) | Film flatness |
|---|---|---|---|---|---|---|---|
| Example 16 | Compound 1-5 | Compound 2-1 | Excellent | O.K | O.K | 0.019/0.04 | O.K |
| Example 17 | Compound 1-5 | Compound 2-1 + 3-ethylbiphenyl (7:3) | Excellent | O.K | O.K | 0.05/0.21 | O.K |
| Example 18 | Compound 1-5 | Compound 2-1 + 2-Isopropyl naphthalene (3:7) | Excellent | O.K | O.K | 0.08/0.16 | O.K |
| Comparative Example 11 | Compound 1-5 | 1-ethylnaphthalene | Excellent | O.K | O.K | 0.25/0.92 | N.G |
| Comparative Example 18 | Compound 1-5 | Benzyl acetate | Excellent | O.K. | N.G | 0.15/0.33 | N.G. |

TABLE 6

| | Functional layer material | Solvent | Solubility | Film image | Discharge stability | Film flatness measurement value (x axis/y axis) | Film flatness |
|---|---|---|---|---|---|---|---|
| Example 19 | Compound 1-6 | Compound 2-1 | Excellent | O.K | O.K | 0.007/0.04 | O.K |
| Example 20 | Compound 1-6 | Compound 2-1 + 3-ethylbiphenyl (7:3) | Excellent | O.K | O.K | 0.03/0.06 | O.K |
| Example 21 | Compound 1-6 | Compound 2-1 + 2-Isopropyl naphthalene (3:7) | Excellent | O.K | O.K | 0.05/0.2 | O.K |
| Example 22 | Compound 1-6 | Compound 2-2 | Excellent | O.K | O.K | 0.03/0.07 | O.K |
| Comparative Example 12 | Compound 1-6 | 1-ethylnaphthalene | Good | O.K | O.K | 0.2/0.84 | N.G |

As shown in Tables 1 to 6, it can be confirmed that Examples 1 to 22 in which the compound represented by Formula 1 and the solvent represented by Formula 2 according to the present specification are used have excellent discharge stability and film flatness as compared to Comparative Examples 1 to 18 in which the solvent represented by Formula 2 is not used. In particular, in Comparative Examples 3, 7, and 9, ink agglomeration occurred, so that the flatness could not be measured.

Although the preferred exemplary embodiments of the present invention have been described above, the present invention is not limited thereto, and various modifications can be made and carried out within the scopes of the claims and the detailed description of the invention, and also fall within the scope of the invention.

The invention claimed is:

1. An ink composition comprising:
a compound represented by the following Formula 1; and
a solvent represented by the following Formula 2:

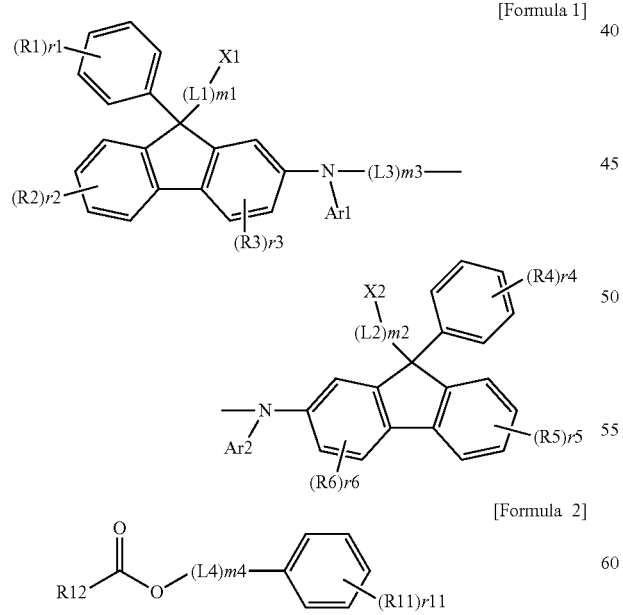

[Formula 1]

[Formula 2]

in Formulae 1 and 2,

L1, L2, and L4 are the same as or different from each other, and are each independently a direct bond; a substituted or unsubstituted alkylene group; a substituted or unsubstituted arylene group; or a substituted or unsubstituted heteroarylene group, L3 is a substituted or unsubstituted arylene group; or a substituted or unsubstituted heteroarylene group, X1 and X2 are the same as or different from each other, and are each independently a photocurable group or a thermosetting group, Ar1 and Ar2 are the same as or different from each other, and are each independently a substituted or unsubstituted aryl group; or a substituted or unsubstituted heteroaryl group, R1 to R6 are the same as or different from each other, and are each independently hydrogen; deuterium; a substituted or unsubstituted alkyl group; a substituted or unsubstituted alkoxy group; a substituted or unsubstituted aryl group; or a substituted or unsubstituted heteroaryl group, R11 is hydrogen; deuterium; or a substituted or unsubstituted alkyl group, R12 is a substituted or unsubstituted alkyl group having 2 or more carbon atoms, m1 to m4 are the same as or different from each other, and are each independently an integer from 1 to 6, when m1 to m4 are each 2 or more, two or more L1's to L4's are each the same as or different from each other, r1, r4, and r11 are the same as or different from each other, and are each independently an integer from 1 to 5, r2 and r5 are the same as or different from each other, and are each independently an integer from 1 to 4, r3 and r6 are the same as or different from each other, and are each independently an integer from 1 to 3, and when r1 to r6 and r11 are each 2 or more, two or more R1's to R6's and R11's are each the same as or different from each other.

2. The ink composition of claim 1, wherein X1 and X2 are the same as or different from each other, and are each independently any one selected from the following structures:

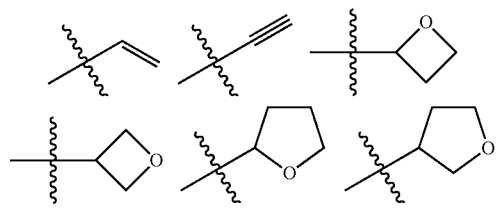

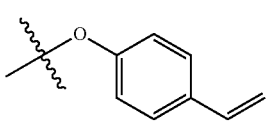
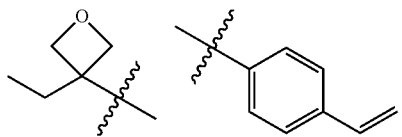

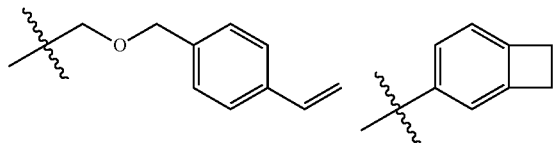
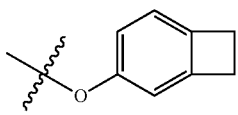

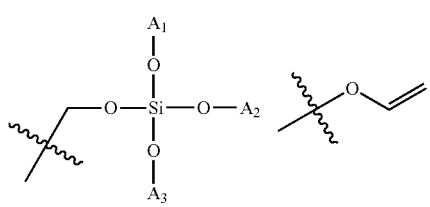

in the structures,

A₁ to A₃ are the same as or different from each other, and are each independently a substituted or unsubstituted alkyl group having 1 to 6 carbon atoms.

3. The ink composition of claim 1, wherein L3 is a substituted or unsubstituted phenylene group, a substituted or unsubstituted biphenylene group, a substituted or unsubstituted terphenylene group, a substituted or unsubstituted naphthylene group, a substituted or unsubstituted phenanthrylene group, or a substituted or unsubstituted fluorenylene group.

4. The ink composition of claim 1, wherein Ar1 and Ar2 are the same as or different from each other, and are each independently a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, a substituted or unsubstituted triphenylene group, or a substituted or unsubstituted fluorenyl group.

5. The ink composition of claim 1, wherein the compound represented by Formula 1 is any one selected from the following compounds 1-1 to 1-6:

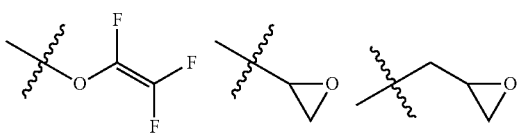

Compound 1-1

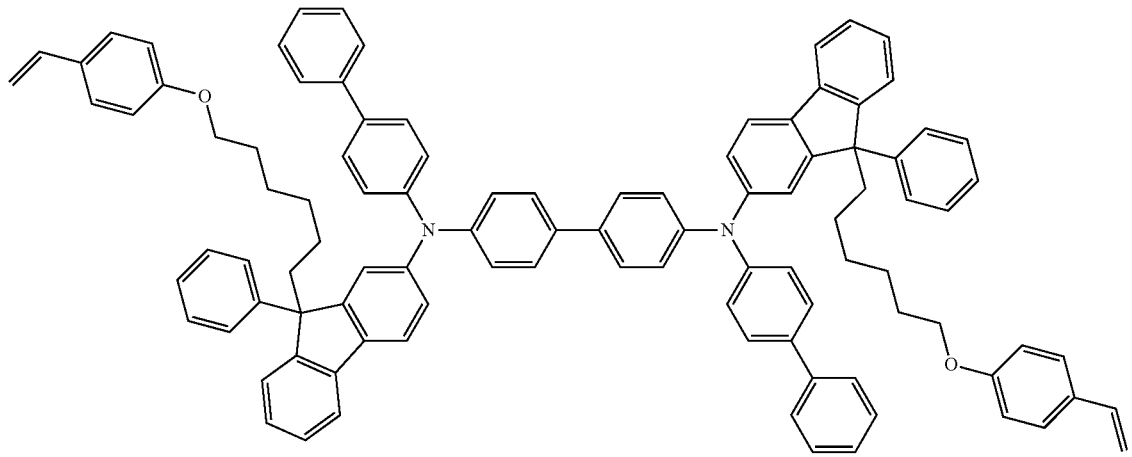

Compound 1-2
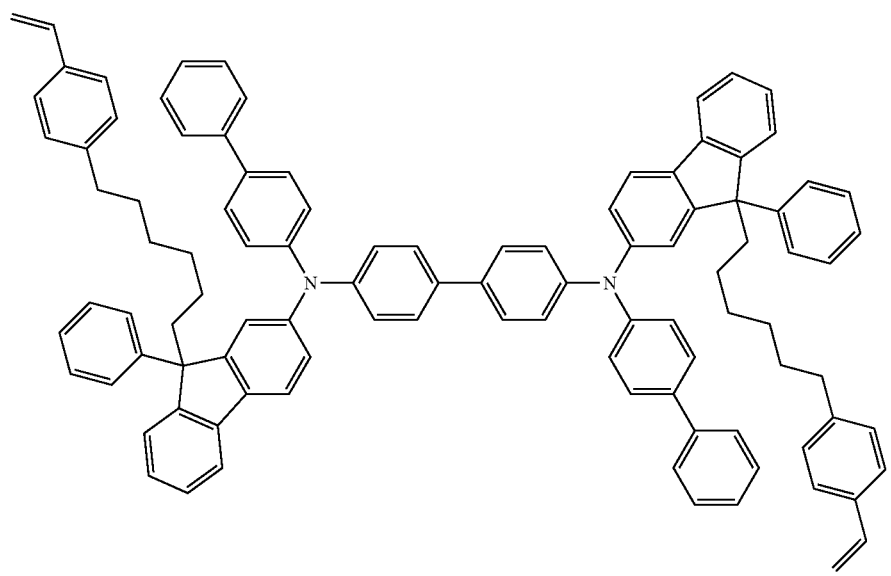
Compound 1-3
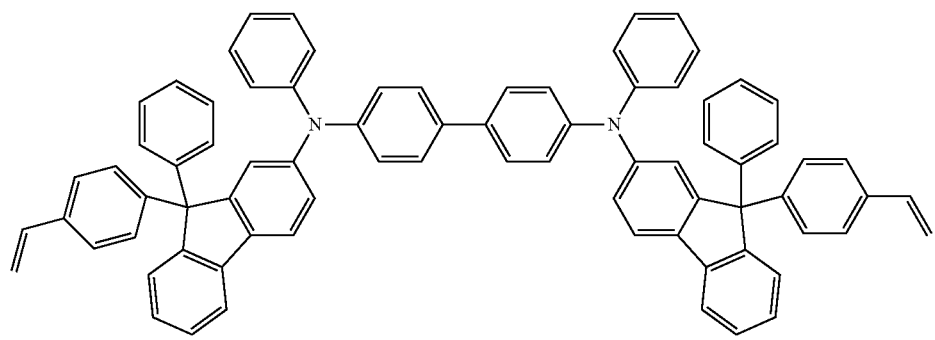
Compound 1-4
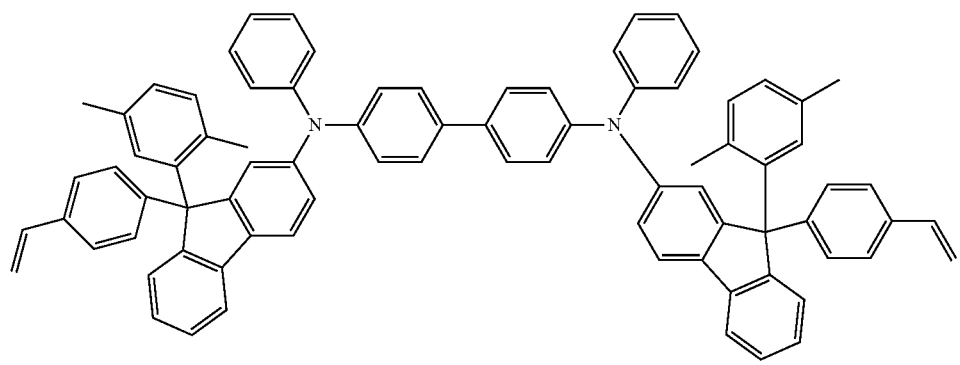

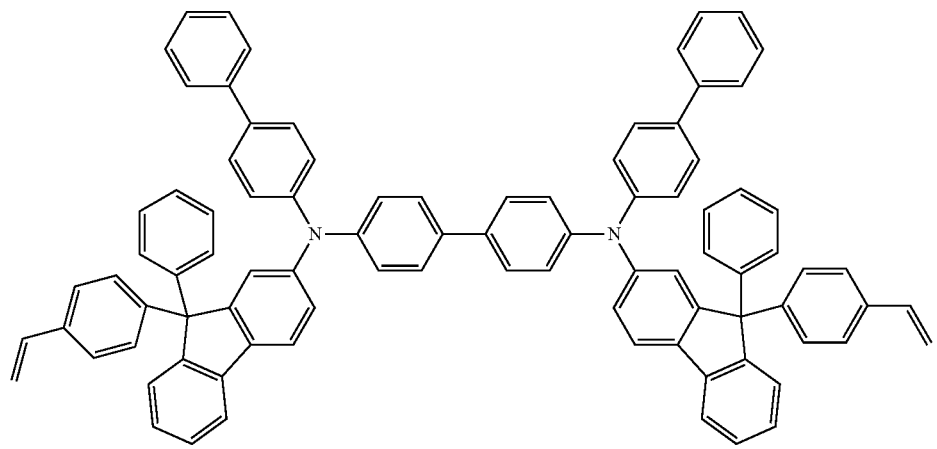

Compoound 1-5

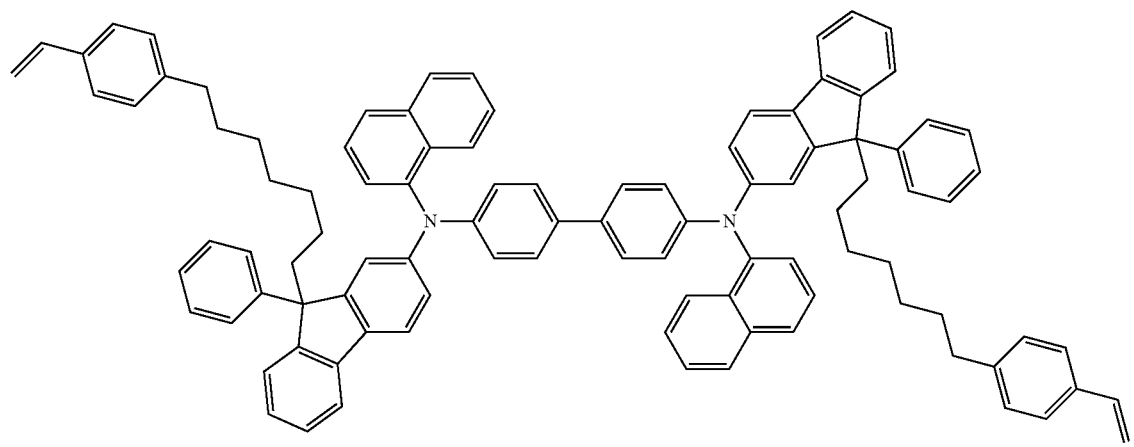

Compound 1-6

6. The ink composition of claim 1, wherein the solvent represented by Formula 2 is any one selected from the following compounds 2-1 to 2-7:

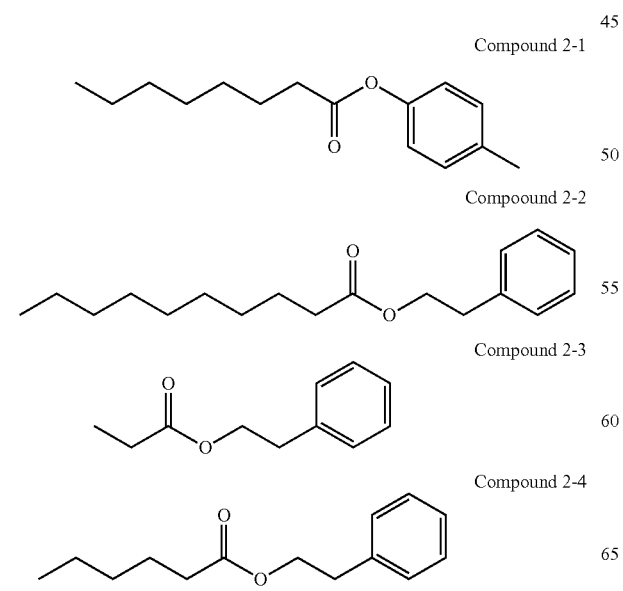

7. The ink composition of claim 1, further comprising: a subsolvent.

8. The ink composition of claim 7, wherein the subsolvent is 3-ethylbiphenyl, 2-isopropylnaphthalene, or 2-phenylethyl alcohol.

9. The ink composition of claim 1, wherein the compound represented by Formula 1 is comprised in an amount of 0.1 part by weight to 10 parts by weight based on 100 parts by weight of the total solvent.

10. The ink composition of claim 1, wherein the ink composition has a viscosity of 2 cP to 20 cP.

11. A method for manufacturing an organic light emitting device, the method comprising:
preparing a substrate;
forming a first electrode or a second electrode on the substrate;
forming an organic material layer having at least one layer on the first electrode or the second electrode; and
forming a second electrode or a first electrode on the organic material layer,
wherein the at least one layer is formed by using the ink composition of claim 1.

12. The method of claim 11, wherein the at least one layer is formed by an inkjet printing method.

13. The method of claim 11, wherein the at least one layer formed by using the ink composition is a light emitting layer.

14. The method of claim 11, wherein the at least one layer formed by using the ink composition is an electron injection layer or an electron transport layer.

15. The method of claim 11, wherein the at least one layer formed by using the ink composition is a hole injection layer, a hole transport layer, or a layer which simultaneously injects or transports holes.

16. The ink composition of claim 1, wherein L1 and L2 the same as or different from each other, and are each independently a substituted or unsubstituted hexylene group, a substituted or unsubstituted heptylene group, or a substituted or unsubstituted octylene group.

17. The ink composition of claim 1, wherein L4 is a substituted or unsubstituted methylene group, a substituted or unsubstituted ethylene group, a substituted or unsubstituted propylene group, a substituted or unsubstituted butylene group, a substituted or unsubstituted pentylene group, or a substituted or unsubstituted hexylene group.

18. The ink composition of claim 1, further comprising:
a p-doping material.

* * * * *